US008361719B2

(12) United States Patent
Jeddeloh et al.

(10) Patent No.: US 8,361,719 B2
(45) Date of Patent: *Jan. 29, 2013

(54) METHODS FOR QUANTITATIVE DETERMINATION OF METHYLATION DENSITY IN A DNA LOCUS

(75) Inventors: Jeffrey A. Jeddeloh, Oakville, MO (US); Nathan D. Lakey, Chesterfield, MO (US)

(73) Assignee: Orion Genomics LLC, St. Louis, MO (US)

( * ) Notice: Subject to any disclaimer, the term of this patent is extended or adjusted under 35 U.S.C. 154(b) by 133 days.

This patent is subject to a terminal disclaimer.

(21) Appl. No.: 12/896,753

(22) Filed: Oct. 1, 2010

(65) Prior Publication Data

US 2012/0100535 A1 Apr. 26, 2012

Related U.S. Application Data

(63) Continuation of application No. 10/971,986, filed on Oct. 21, 2004, now Pat. No. 7,910,296.

(60) Provisional application No. 60/561,721, filed on Apr. 12, 2004, provisional application No. 60/561,563, filed on Apr. 12, 2004, provisional application No. 60/513,426, filed on Oct. 21, 2003.

(51) Int. Cl.
C12Q 1/66 (2006.01)
C12P 19/34 (2006.01)
C07H 21/04 (2006.01)

(52) U.S. Cl. ...... 435/6.1; 435/6.12; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 5,405,760 | A | 4/1995 | Raleigh et al. |
| 5,786,146 | A | 7/1998 | Herman et al. |
| 5,854,033 | A | 12/1998 | Lizardi |
| 5,871,917 | A | 2/1999 | Duffy |
| 5,912,147 | A | 6/1999 | Stoler et al. |
| 6,200,756 | B1 | 3/2001 | Herman et al. |
| 6,265,171 | B1 | 7/2001 | Herman et al. |
| 6,312,906 | B1 | 11/2001 | Cass et al. |
| 6,331,393 | B1 | 12/2001 | Laird et al. |
| 6,383,754 | B1 | 5/2002 | Kaufman et al. |
| 6,498,013 | B1 | 12/2002 | Velculescu et al. |
| 6,605,432 | B1 | 8/2003 | Huang |
| 6,777,187 | B2 | 8/2004 | Makarov et al. |
| 7,459,274 | B2 | 12/2008 | Lakey et al. |
| 7,901,880 | B2 | 3/2011 | Jeddeloh et al. |
| 2002/0123053 | A1 | 9/2002 | Luo et al. |
| 2003/0017454 | A1 | 1/2003 | Sukumar et al. |
| 2003/0099997 | A1 | 5/2003 | Bestor |
| 2003/0129602 | A1 | 7/2003 | Huang |
| 2003/0143599 | A1 | 7/2003 | Makarov et al. |
| 2003/0148290 | A1 | 8/2003 | Cottrell |
| 2003/0165923 | A1 | 9/2003 | Li et al. |
| 2003/0175828 | A1 | 9/2003 | Lazar |
| 2003/0180779 | A1 | 9/2003 | Lofton-Day et al. |
| 2004/0209299 | A1 | 10/2004 | Pinter et al. |
| 2004/0234960 | A1 | 11/2004 | Olek et al. |
| 2005/0153316 | A1 | 7/2005 | Jeddeloh et al. |

FOREIGN PATENT DOCUMENTS

| | | |
|---|---|---|
| WO | WO 00/26401 | 5/2000 |
| WO | WO 00/43780 | 7/2000 |
| WO | WO 01/68807 | 9/2001 |
| WO | WO 01/75172 | 10/2001 |
| WO | WO 01/83751 | 11/2001 |
| WO | WO 01/96608 | 12/2001 |
| WO | WO 02/18649 | 3/2002 |
| WO | WO 02/38811 | 5/2002 |
| WO | WO 02/059347 | 8/2002 |
| WO | WO 02/103042 | 12/2002 |
| WO | WO 03/002752 | 1/2003 |
| WO | WO 03/023065 | 3/2003 |
| WO | WO 03/025215 | 3/2003 |
| WO | WO 03/027259 | 4/2003 |
| WO | WO 03/050242 | 6/2003 |
| WO | WO 03/066895 | 8/2003 |
| WO | WO 03/076666 | 9/2003 |
| WO | WO 03/078966 | 9/2003 |
| WO | WO 2004/031402 | 4/2004 |

OTHER PUBLICATIONS

Adorjan, Peter et al.; "Tumour class prediction and discovery by microarray-based DNA methylation analysis"; Nucleic Acids Research, 2002, vol. 30, No. 5 e21, 9 pages.
Badal, Vinay et al.; "CpG Methylation of Human Papillomavirus Type 16 DNA in Cervical Cancer Cell Lines and in Clinical Specimens: Genomic Hypomethylation Correlates with Carcinogenic Progression"; 2003, Journal of Virology, vol. 77, No. 11, pp. 6227-6234.
Burman et al. Am. J. Hum. Genet. 1999, 65:1375-1386.
Burman Robert W. et al.; "Hypomethylation of an Expanded FMR1 Allele Is Not Associated with a Global DNA Methylation Defect"; Am. J. Hum. Genet., 1999, vol. 65, pp. 1375-1386.
Butkus, et al., "Cleavage of methylated CCCGGG sequences containing either N4-methylcytosine or 5- methylcytosine with Mspl, Hpall, Smal, Xmal and Cfr-9I restriction endonucleases," 1987, Nucleic Acids Res., vol. 15(17), pp. 7091-7102.
Caldas, Carlos et al.; "Frequent somatic mutations and homozygous deletions of the p16 (MTS1) gene in pancreatic adenocarcinoma"; Nature Genetics, 1994, vol. 8, pp. 27-32.
Chen, Chuan-Mu et al.; "Methylation Target Array for Rapid Analysis of CpG Island Hypermethylation in Multiple Tissue Genomes"; 2003, American Journal of Pathology, vol. 163, No. 1, pp. 37-45.
Chotai, et al., "A rapid, PCR based test for differential molecular diagnosis of Prader-Willi and Angelman syndromes," 1998, J. Med. Genen., vol. 35, pp. 472-475. Chu et al. (J. Urology, 2002, vol. 167, pp. 1854-1858).
Chu, Da-Chang et al.; "The use of Real-Time Quantitative Polymerase Chain Reaction to Detect Hypermethylation of the CPG Islands in the Promoter Region Flanking the GSTP1 Gene to Diagnose Prostate Carcinoma"; 2002, The Journal of Urology, vol. 167, pp. 1854-1858.
Craig, B.A. et al.; "Designing Microarrays"; Applied Statistics in Agriculture, pp. 159-164.
Dahl, et al., "DNA methylation analysis techniques," 2003, Biogerontology, vol. 4, pp. 233-250.
Eads, Cindy A. et al.; "MethyLight: a high-throughput assay to measure DNA methylation"; Nucleic Acids Research, 2000, vol. 28, No. 8, e32, 8 pages.
Fantappie, et al., "Lack of DNA methylation in Schistosoma mansoni," 2001, Experimental Parasitology, vol. 98, pp. 162-166.

(Continued)

Primary Examiner — Sarae Bausch
(74) Attorney, Agent, or Firm — Kilpatrick Townsend & Stockton LLP

(57) ABSTRACT

The present invention is a novel method of determining the average DNA methylation density of a locus of interest within a population of DNA fragments.

19 Claims, 20 Drawing Sheets

OTHER PUBLICATIONS

Field, Linda M.; "Methylation and expression of amplified esterase genes in the aphid Myzus persicae (Sulzer)"; 2000, Biochem. J., vol. 349, pp. 863-868.

Fraga, Mario F. et al.; "DNA Methylation: A Profile of Methods and Applications"; 2002, BioTechniques, vol. 33, pp. 632-649.

Frigola, Jordi et al.; Methylome profiling of cancer cells by amplification of inter-methylated sites (AIMS); Nucleic Acids Research, 2002, vol. 30, No. 7, e28, 7 pages.

Genc, B. et al.; "Identification of disease associated genes and tumour class prediction by genome wide microarray-based DNA methylation scanning"; The American Journal of Human Genetics, 2001, vol. 69, No. 4, 1 page abstract.

Hatada, Izuho et al.; "A microarray-based method for detecting methylated loci"; J. Hum. Genet, 2002, Vo. 47, pp. 448-451.

Herman, James G. et al.; "Methylation-specific PCR: A novel PCR assay for methylation status of CpG islands"; Proc. Natl. Acad. Sci., 1996, vol. 93, pp. 9821-9826.

Horike, S. et al.; "Targeted disruption of the human LITI locus defines a putative imprinting control element playing an essential role in Beckwith-Wiedemann syndrome"; 2000, Human Molecule Genetics, vol. 9, pp. 2075-2083.

Huang, Tim Hui-Ming et al.; "Methylation profiling of CpG islands in human breast cancer cells"; Human Molecular Genetics, 1999, vol. 8, No. 3, pp. 459-470.

Kinzler, Kenneth W. et al.; "Whole genome PCR: application to the identification of sequences bound by gene regulatory proteins"; 1989, Nucleic Acids Research, vol. 17, No. 10, pp. 3645-3653.

Lapidus, Rena G. et al.; "Methylation of Estrogen and Progesterone Receptor Gene 5' CpG Islands Correlates with Lack of Estrogen and Progesterone Recptor Gene Expression in Brest Tumors"; 1996, Clinical Cancer Research, vol. 2, pp. 805-810.

Lewin, Jorn et al.; "Quantitative DNA methylation analysis based on four-dye trace data from direct sequencing of PCR amplificates"; 2004, Bioinformatics, vol. 20, No. 0, pp. 1-8.

Li, Long-Cheng et al.; "MethPrimer: designing promers for methylation PCRs"; 2002, Bioinformatics, vol. 18, No. 11, pp. 1427-1431.

McClelland, Michael et al.; "Effect of site-specific modification on restriction endonucleases and DNA modification methyltransferases"; Nucleic Acids Research, 1994, vol. 22, No. 17, pp. 3640-3659.

McGrew, et al., "Quantitation of genomic methylation using ligation-mediated PCR," 1993, BioTechniques, vol. 15(4), pp. 722-724, 726 and 728-729.

McrBC—M0272—NEB Restriction Endonucleases; http://www.neb.com/neb/products/res.sub.—enzymes/272.html, 3 pages.

"McrBC"; Technical Bulletin, 2001, New England Biolabs, Inc., 2 pages.

Menon, et al., "Identification and characterization of a novel transcript of the murine growth hormone receptor gene exhibiting development- and tissue-specific expression," 2001, Mol. Cell. Endocrinol., vol. 172, pp. 135-146.

Okamoto, Keisei et al.; "Epigenetic changes at the insulin-like growth factor II/H19 locus in developing kidney is an early event in Wilms tumorigenesis"; Proc. Natl. Acad. Sci., 1997, vol. 94, pp. 5367-5371.

Pham, et al.; "Uteroplacental insufficiency increases apoptosis and alters p53 gene methylation in the full-term IUGR rat kidney"; 2003, American Journal of Physiology, vol. 285(5) part 2, pp. R962-R970.

Schutte, Mieke et al.; "Abrogation of the Rb/p16 Tumor-suppressive Pathway in Virtually All Pancreatic Carcinomas"; Cancer Research, 1997, vol. 57, pp. 3126-3130.

Sheikhha, Mohammad H. et al.; "High level of microsatellite instability but not hypermethylation of mismatch repair genes in therapy-related and secondary acute myeloid leukaemia and myelodysplastic syndrome"; 2002, British Journal of Haematology, vol. 117, pp. 359-365.

Singal, Rakesh et al.; "Microsoft Word Macro for Analysis of Cytosine Methylation by the Bisulfite Deamination Reaction"; 2001, BioTechniques, vol. 30, pp. 116-120.

Steigerwald, Sabine D. et al.; "Ligation-mediated PCR improves the sensitivity of methylation analysis by restriction enzymes and detection of specific DNA strand breaks"; Nucleic Acids Research, 1990, vol. 18, No. 6, pp. 1435-1439.

Strathdee, G. et al.; "A role for methylation of the hMLH1 promoter in loss of hMLH1 expression and drug resistance in ovarian cancer"; 1999, Oncogene, vol. 18, pp. 2335-2341.

Sutton, I.J. et al.; "Limb girdle and facial weakness in female carriers of X-linked myotubular myopathy mutations"; 2001, Neurology, vol. 57, pp. 900-902.

Tanabe, Chilkako et al.; "Evaluation of a Whole-Genome Amplification Method Based on Adaptor-Ligation PCR of Randomly Sheared Genomic DNA"; 2003, Genes, Chromosomes & Cancer, vol. 38, pp. 168-176.

Tompa, Rachel et al.; "Genome-Wide Profiling of DNA Methylation Reveals Transposon Targets of Chromomethylase3"; Current Biology, 2002, vol. 12, pp. 65-68.

Toyota, Minoru et al.; "Identification of Differentially Methylated Sequences in Colorectal Cancer by Methylated CpG Island Amplification"; Cancer Research, 1999, vol. 59, pp. 2307-2312.

Trinh et al. (Methods (2001) 25:456-462).

Uhlmann, Karen et al.; "Evaluation of a potential epigenetic biomarker by quantitative methyl-single nucleotide polymorphism analysis"; 2002, Electrophoresis, vol. 23, pp. 4072-4079.

Wang, C.H. et al.; "Autism DNA methylation profiling using CpG microarrays"; The American Journal of Human Genetics, 2001, vol. 69, No. 4, 1 page abstract.

Wei, Susan H. et al.; "Methylation Microarray Analysis of Late-Stage Ovarian Carcinomas Distinguishes Progression-free Survival in Patients and Identifies Candidate Epigenetic Markers"; Clinical Cancer Research, 2002, vol. 8, pp. 2246-2252.

Yamada, Yoichi et al.; "A comprehensive analysis of CpG islands reveals methylation imprints on human chromosome 21"; HGM2002 Workshop Abstract No. 13, 1 page.

Yamada, Yoichi et al.; "A comprehensive analysis of CpG islands reveals methylation imprints on human chromosome 21"; HGM2002 Poster No. 89, 1 page.

Yamada, Yoichi et al.; "A comprehensive analysis of Allelic Methylation Status of CpG Islands on Human Chromosome 21q"; 2004, Genome Research, pp. 247-266.

Yan, Pearlly S. et al. "CpG Island Arrays: An Application toward Deciphering Epigenetic Signatures of Breast Cancer"; 2000, Clinical Cancer Research, vol. 6, pp. 1432-1438.

Xiong, et al., "Patterns of cytosine methylation in an elite rice hybrid and its parental lines, detected by a methylation-sensitive amplification polymorphism technique," 1999, Mol. Gen. Genet., vol. 261, pp. 439-446.

Applied Biosystems: User Bulletin #2—ABI Prism 7700 Sequence Detection System. 36 pages. Dec. 11, 1997.

Humane Genome Center: Laboratory of Genome Database, pp. 128-132.

Humane Genome Center: Laboratory of Genome Structure Analysis, pp. 133-135.

Humane Genome Center: Laboratory DNA. Information Analysis, pp. 136-149.

Humane Genome Center: Laboratory of Sequence Analysis, pp. 150-152.

Humane Genome Center: Laboratory of Functional Genomics, pp. 153-156.

HGM2002; Seventh International Human Genome Meeting, Apr. 2002.

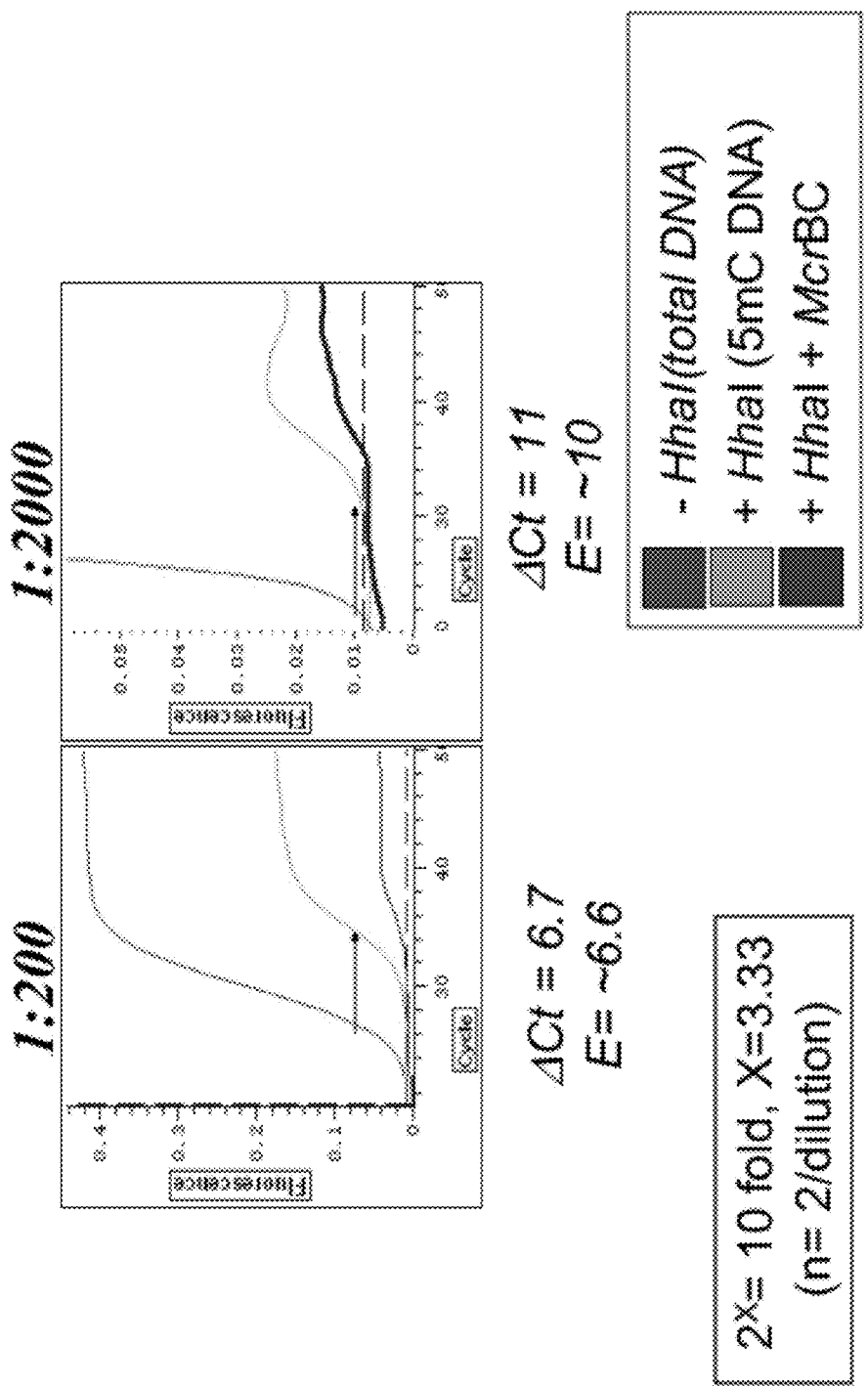

Figure 5

- How many cellular equivalents did we detect?
  - 20ng of genomic DNA total is ~ 2,764 cellular equiv
  - The yield from a typical biopsy core ~1 ug

| Dilution | CE Meth | CE Unmeth | CE Total |
|---|---|---|---|
| 1:2 | ~1,400 | 1,364 | 2,764 |
| 1:20 | ~140 | 2,624 | 2,764 |
| 1:200 | ~14 | 2,750 | 2,764 |
| 1:2,000 | ~1.4 | 2,762 | 2,764 | a) BAC with sparse Meth
 - Hha digested,
 - 1x McrBC
 - qPCR of biomarker b) BAC with sparse Meth
 - Hha digested,
 - 5x McrBC
 - qPCR of biomarker c) BAC with sparse Meth
 - Hha digested,
 - 25x McrBC
 - qPCR of biomarker a) BAC with dense Meth.
 - Hha digested,
 - 1x McrBC
 - qPCR of biomarker b) BAC with dense Meth.
 - Hha digested,
 - 5x McrBC
 - qPCR of biomarker c) BAC with dense Meth.
 - Hha digested,
 - 25x McrBC
 - qPCR of biomarker

Figure 16
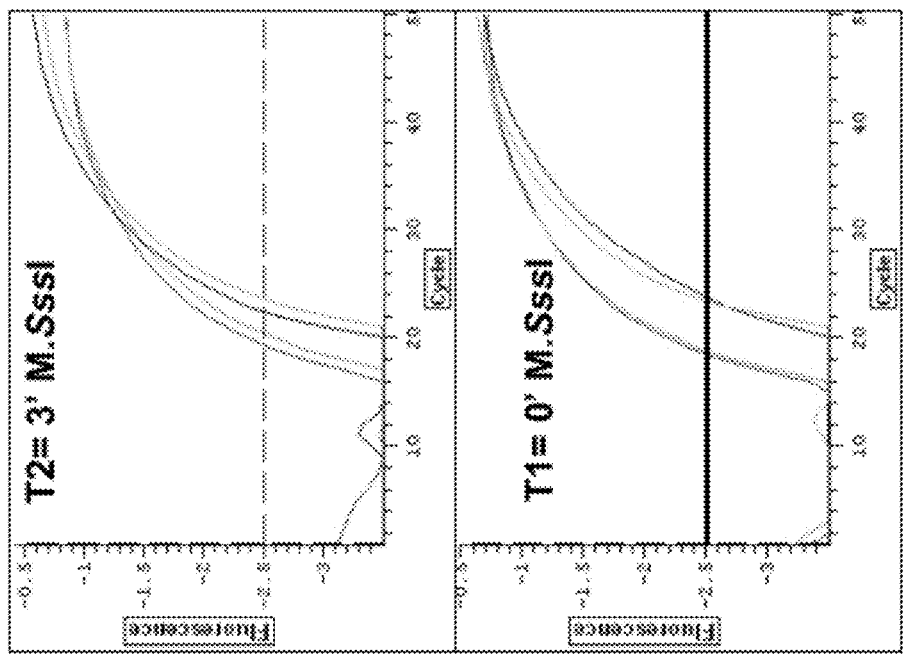
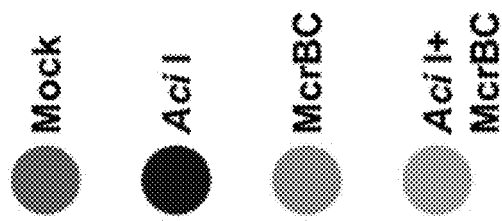
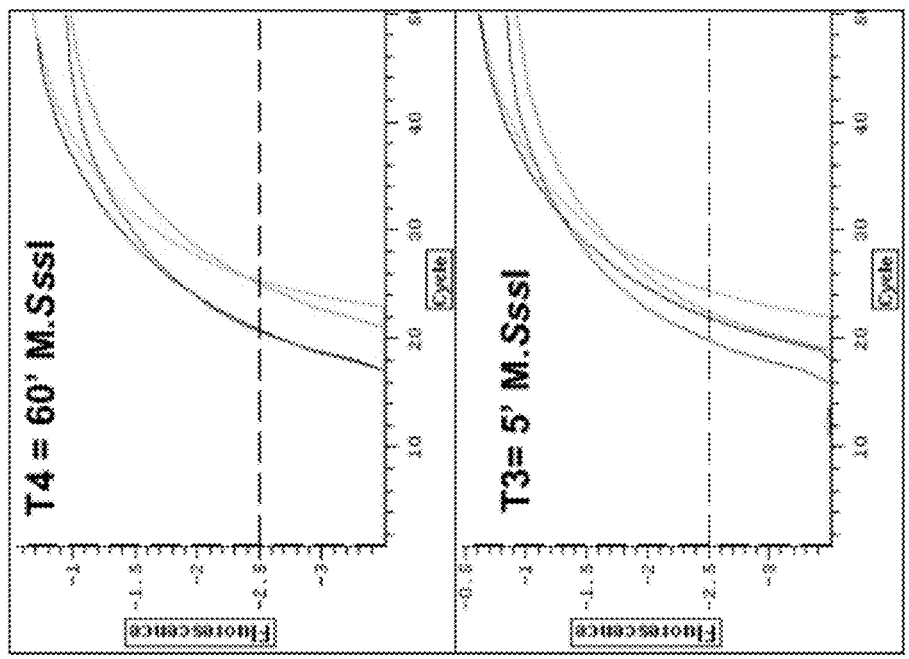

SEQUENCE LISTING

```
<160> NUMBER OF SEQ ID NOS: 7

<210> SEQ ID NO 1
<211> LENGTH: 703
<212> TYPE: DNA
<213> ORGANISM: Homo sapiens
<220> FEATURE:
<223> OTHER INFORMATION: portion of human cyclin dependent kinase
      inhibitor CDKN2A (p16) promoter methylated in vitro with M.SssI

<400> SEQUENCE: 1
cagggcgtcg ccaggaggag gtctgtgatt acaaacccct tctgaaaact ccccaggaag      60 cctcccttt ttccggagaa tcgaagcgct acctgattcc aattccctg caaacttcgt      120 cctccagagt cgcccgccat ccctgctcc cgctgcagac cctctaccca cctggatcgg      180
cctccgaccg taactattcg gtgcgttggg cagcgccccc gcctccagca gcgcccgcac      240
ctcctctacc cgaccccggg ccgcggccgt ggccagccag tcagccgaag gctccatgct      300
gctccccgcc gccggctcca tgctgctccc cgccgccgc tgcctgctct mccctctcc      360 gcagccgccg agcgcacgcg gtccgcccca ccctctggtg accagccagc ccctcctctt      420
tcttcctccg gtgctggcgg aagagccccc tccgaccctg tccctcaaat cctctggagg      480
gaccgcggta tctttccagg caaggggacg cygtgagcga gtgctcggag gaggtgctat      540
taactccgag cacttagcga atgtggcacc cctgaagtcg ccccaggttg ggtctccccc      600
gggggcacca gccggaagca gccctcgcca gagccagcgt tggcaaggaa ggaggactgg      660
gctcctcccc acctgccccc cacaccgccc tccggcctcc ctg                        703

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Forward
      primer specific for region upstream of human CDKN2A (p16) gene

<400> SEQUENCE: 2
cggggacgcg agcagcacca gaat                                            24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:Reverse
```

-continued primer specific for region upstream of human CDKN2A (p16) gene

<400> SEQUENCE: 3
cgcccccacc cccaccacca t                                      21

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:quantitative
      PCR F primer

<400> SEQUENCE: 4
cagggcgtcg ccaggaggag gtctgtgatt                             30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:quantitative
      PCR R primer

<400> SEQUENCE: 5
ggcgctgccc aacgcaccga atagttacgg                             30

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Sorghum
      bicolor kafirin gene amplicon PCR amplification forward primer

<400> SEQUENCE: 6
ctccttgcgc tccttgctct ttc                                    23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Sorghum
      bicolor kafirin gene amplicon PCR amplification reverse primer

<400> SEQUENCE: 7
gctgcgctgc gatggtctgt                                        20

METHODS FOR QUANTITATIVE DETERMINATION OF METHYLATION DENSITY IN A DNA LOCUS

CROSS-REFERENCE TO RELATED PATENT APPLICATIONS

The present application is a continuation of U.S. patent application Ser. No. 10/971,986, filed Oct. 21, 2004, now U.S. Pat. No. 7,901,880, issued Mar. 8, 2011, which claims benefit of priority to U.S. Provisional Patent Application No. 60/561,721, filed Apr. 12, 2004, U.S. Provisional Patent Application No. 60/561,563, filed Apr. 12, 2004, and U.S. Provisional Patent Application No. 60/513,426, filed Oct. 21, 2003, each of which are incorporated by reference in their entirety for all purposes.

BACKGROUND OF THE INVENTION

Human cancer cells typically contain somatically altered genomes, characterized by mutation, amplification, or deletion of critical genes. In addition, the DNA template from human cancer cells often displays somatic changes in DNA methylation. See, e.g., E. R. Fearon, et al, *Cell* 61:759 (1990); P. A. Jones, et al., *Cancer Res.* 46:461 (1986); R. Holliday, *Science* 238:163 (1987); A. De Bustros, et al., *Proc. Natl. Acad. Sci. USA* 85:5693 (1988); P. A. Jones, et al., *Adv. Cancer Res.* 54:1 (1990); S. B. Baylin, et al., *Cancer Cells* 3:383 (1991); M. Makos, et al., *Proc. Natl. Acad Sci. USA* 89:1929 (1992); N. Ohtani-Fujita, et al., *Oncogene* 8:1063 (1993).

DNA methylates transfer methyl groups from the universal methyl donor S-adenosyl methionine to specific sites on the DNA. Several biological functions have been attributed to the methylated bases in DNA. The most established biological function is the protection of the DNA from digestion by cognate restriction enzymes. This restriction modification phenomenon has, so far, been observed only in bacteria.

Mammalian cells, however, possess a different methylase that exclusively methylates cytosine residues on the DNA that are 5' neighbors of guanine (CpG). This methylation has been shown by several lines of evidence to play a role in gene activity, cell differentiation, tumorigenesis, X-chromosome inactivation, genomic imprinting and other major biological processes (Razin, A., H., and Riggs, R. D. eds. in *DNA Methylation Biochemistry and Biological Significance*, Springer-Verlag, N.Y., 1984).

In eukaryotic cells, methylation of cytosine residues that are immediately 5' to a guanosine, occurs predominantly in CG poor loci (Bird, A., *Nature* 321:209 (1986)). In contrast, discrete regions of CG dinucleotides called CpG islands remain unmethylated in normal cells, except during X-chromosome inactivation and parental specific imprinting (Li, et al., *Nature* 366:362 (1993)) where methylation of 5' regulatory regions can lead to transcriptional repression. For example, de novo methylation of the Rb gene has been demonstrated in a small fraction of retinoblastomas (Sakai, et al., *Am. J. Hum. Genet.*, 48:880 (1991)), and a more detailed analysis of the VHL gene showed aberrant methylation in a subset of sporadic renal cell carcinomas (Herman, et al., *Proc. Natl. Acad. Sci. U.S.A.*, 91:9700 (1994)). Expression of a tumor suppressor gene can also be abolished by de novo DNA methylation of a normally unmethylated 5' CpG island. See, e.g., Issa, et al., *Nature Genet.* 7:536 (1994); Merlo, et al., *Nature Med.* 1:686 (1995); Herman, et al., *Cancer Res.*, 56:722 (1996); Graff, et al., *Cancer Res.*, 55:5195 (1995); Herman, et al., *Cancer Res.* 55:4525 (1995).

Identification of the earliest genetic changes in tumorigenesis is a major focus in molecular cancer research. Diagnostic approaches based on identification of these changes can allow implementation of early detection strategies, tumor staging and novel therapeutic approaches targeting these early changes, leading to more effective cancer treatment. The present invention addresses these and other problems.

BRIEF SUMMARY OF THE INVENTION

The present invention provides methods for quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some embodiments, the quantifying step comprises a quantitative amplification. In some embodiments, the quantity of the amplified product is compared to a standard curve.

In some embodiments, the quantifying step comprises the direct detection of intact copies of locus with hybrid capture.

In some embodiments, the amplifying step comprises hybridizing two oligonucleotide primers to DNA flanking the locus to produce an amplification product corresponding to the uncleaved locus of genomic DNA between the primers.

In some embodiments, the control value represents the quantity of an amplification product of a DNA sample having a known or predicted number of methylated nucleotides.

In some embodiments, the restriction enzyme is a methylation-sensitive restriction enzyme. In some embodiments, the methylation-sensitive restriction enzyme is selected from the group consisting of Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, ClaI Eae I, Eag I, Fau I, Fse I, Hha I, HinP1 I, HinC II, Hpa II, Hpy99 I, HpyCH4 IV, Kas I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I.

In some embodiments, the restriction enzyme is a methylation-dependent restriction enzyme. In some embodiments, the restriction enzyme is a methyl-cytosine-dependent restriction enzyme. In some embodiments, the restriction enzyme is McrBC. In some embodiments, the restriction enzyme is a methyl-adenosine-dependent restriction enzyme. In some embodiments, the restriction enzyme is DpnI.

In some embodiments, the methylation-sensitive or methylation dependent restriction enzyme is contacted to the portion under conditions to allow for only a partial digest of the portion.

In some embodiments, the method comprises separating the genomic DNA into at least two equal portions; contacting one portion with a methylation-sensitive or methylation dependent restriction enzyme and contacting a second portion with the isoschizomeric partner of the restriction enzyme, amplifying the locus of genomic DNA in each portion in a step comprising hybridizing two oligonucleotide primers to DNA flanking the locus; quantifying the amplification product; and comparing the quantity of amplified products from the two portions.

In some embodiments, the method further comprises contacting the genomic DNA with an agent that modifies unmethylated cytosine before the amplifying step, and at least one of the two oligonucleotide primers distinguishes between modified unmethylated and methylated DNA in the genomic DNA.

In some embodiments, the method further comprises contacting the DNA with at least one methylation-sensitive restriction enzyme or methylation-dependent restriction enzyme before the genomic DNA is contacted with an agent that modifies unmethylated cytosine. In some embodiments, the genomic DNA is contacted with a mixture of at least two different methylation-dependent or methylation-sensitive restriction enzymes.

In some embodiments, the agent is sodium bisulfite.

In some embodiments, the amplified product is quantified using quantitative PCR.

In some embodiments, the control value is generated by contacting DNA comprising a control locus with a methylation-dependent or methylation-sensitive restriction enzyme; amplifying the control locus; and determining the quantity of the amplified product. In some embodiments, the control locus is known or predicted to be unmethylated.

In some embodiments, the control value comprises a known number of methylated nucleotides. In some embodiments, the genomic DNA is from a human. In some embodiments, the method is performed to detect the presence or absence of cancer cells in a subject.

In some embodiments, the quantifying step comprises detecting a probe that hybridizes to the amplification product. In some embodiments, the probe comprises a detectable fluorescent moiety.

In some embodiments, the quantifying step comprises the direct detection of intact copies of locus with hybrid capture.

In some embodiments, the DNA is from an animal. In some embodiments, the animal is a human.

In some embodiments, the genomic DNA is from a tissue selected from the group consisting of brain tissue, colon tissue, urogenital tissue, lung tissue, renal tissue, hematopoietic tissue, breast tissue, thymus tissue, testis tissue, ovarian tissue, uterine tissue and blood.

In some embodiments, the genomic DNA is from an organism selected from the group consisting of plants, fungi and bacteria.

The present invention also provides methods of calculating the relative methylation density for a target locus in a DNA sample. In some embodiments, the methods comprise
i. contacting the DNA sample with a methylation-dependent restriction enzyme under conditions that allow for at least some copies of potential restriction enzyme cleavage sites in the locus to remain uncleaved to obtain a population of nucleic acids in which at least some methylated copies of the locus are fragmented, or
contacting the DNA sample with a methylation-sensitive restriction enzyme under conditions that allow for at least some copies of potential restriction enzyme cleavage sites in the locus to remain uncleaved to obtain a population of nucleic acids in which at least some unmethylated copies of the locus are fragmented;
ii. quantifying the number of intact copies of the locus in the DNA using hybrid capture; and
iii. determining the relative methylation density for the locus by comparing the hybrid capture signal of a portion of a sample to the hybrid capture signal of a different portion of the sample or to a control value (as described herein).

The present invention also provides methods of calculating the relative methylation density for a target locus in a DNA sample. In some embodiments, the methods comprise
i. contacting the DNA sample with a methylation-dependent restriction enzyme under conditions that allow for at least some copies of potential restriction enzyme cleavage sites in the locus to remain uncleaved to obtain a population of nucleic acids in which at least some methylated copies of the locus are fragmented, or
contacting the DNA sample with a methylation-sensitive restriction enzyme under conditions that allow for at least some copies of potential restriction enzyme cleavage sites in the locus to remain uncleaved to obtain a population of nucleic acids in which at least some unmethylated copies of the locus are fragmented;
ii. quantitatively amplifying intact copies of the locus in the DNA sample after the contacting steps;
iii. identifying the cycle threshold (Ct) value for the amplified portion from the DNA sample; and,
iv. determining the relative methylation density for the target locus by calculating the difference ($\Delta$Ct) between the Ct of the DNA sample and a control Ct value, wherein $2^{|\Delta Ct|}$ equals, or is proportional to the relative methylation density between the DNA sample and the control.

In some embodiments, the control Ct is calculated by steps comprising
i. contacting a control DNA sample with a methylation-dependent restriction enzyme under conditions that allow for at least some copies of potential restriction enzyme cleavage sites in the locus to remain uncleaved to obtain a population of nucleic acids in which at least some methylated copies of the locus are fragmented, or
contacting the control DNA sample with a methylation-sensitive restriction enzyme under conditions that allow for at least some copies of potential restriction enzyme cleavage sites in the locus to remain uncleaved to obtain a population of nucleic acids in which at least some unmethylated copies of the locus are fragmented;
ii. amplifying intact copies of the locus in the control DNA sample after the contacting steps; and,
iii. identifying the cycle threshold (Ct) value for the amplified portion from the control DNA sample.

In some embodiments, the amplifying step comprises hybridizing two oligonucleotide primers to DNA flanking the locus to produce an amplification product corresponding to the uncleaved locus of genomic DNA between the primers. In some embodiments, the restriction enzyme is a methylation-sensitive restriction enzyme. In some embodiments, the methylation-sensitive restriction enzyme is selected from the group consisting of Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, ClaI, Eae I, Eag I, Fau I, Fse I, Hha I, HinP1 I, HinC II, Hpa II, Hpy99 I, HpyCH4 IV, Kas I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I.

In some embodiments, the methylation-sensitive restriction enzyme does not cut when an adenosine within the recognition sequence is methylated at position N6. In some embodiments, the methylation-sensitive restriction enzyme is Mbo I.

In some embodiments, the restriction enzyme is a methylation-dependent restriction enzyme. In some embodiments, the restriction enzyme is a methyl-cytosine-dependent restriction enzyme. In some embodiments, the restriction enzyme is McrBC, McrA, and MrrA. In some embodiments, the restriction enzyme is a methyl-adenosine-dependent restriction enzyme. In some embodiments, the restriction enzyme is DpnI.

In some embodiments, the methylation-sensitive or methylation dependent restriction enzyme is contacted to the portion under conditions to allow for only a partial digest of the portion.

The present invention also provides kits for quantifying the average methylation density in a locus of genomic DNA. In some embodiments, the kit comprises a methylation-dependent restriction enzyme or a methylation sensitive restriction enzyme; a control DNA molecule comprising a pre-determined number of methylated nucleotides; and control oligonucleotide primers that hybridize to the control DNA molecule.

In some embodiments, the restriction enzyme is a methylation-sensitive restriction enzyme. In some embodiments, the restriction enzyme is a methylation-dependent restriction enzyme. In some embodiments, the restriction enzyme is a methyl-cytosine-dependent restriction enzyme. In some embodiments, the restriction enzyme is McrBC.

In some embodiments, the kit further comprises target oligonucleotide primers that hybridize to a pre-determined locus of human genomic DNA. In some embodiments, at least one target oligonucleotide primer distinguishes between modified unmethylated and methylated DNA in human genomic DNA. In some embodiments, the kit comprises a plurality of DNA molecules comprising different pre-determined numbers of methylated nucleotides. In some embodiments, the kit further comprises reagents sufficient to support the activity of the restriction enzyme. In some embodiments, the kit further comprises a thermostable DNA polymerase. In some embodiments, the kit further comprises an agent that modifies unmethylated cytosine. In some embodiments, the kit further comprises a detectably-labeled oligonucleotide. In some embodiments, the kit comprises hybrid capture reagents.

BRIEF DESCRIPTION OF THE DRAWINGS

FIGS. 1A and 1B illustrate results of amplification of DNA at different methylated:unmethylated dilutions.

FIG. 5 illustrates results from different methylated:unmethylated dilutions.

FIG. 16 illustrates data demonstrating that methylation-dependent (i.e., McrBC) and methylation-sensitive (i.e., Aci I) restriction enzymes distinguish different methylation densities at a DNA locus.

DEFINITIONS

Figure 1A:
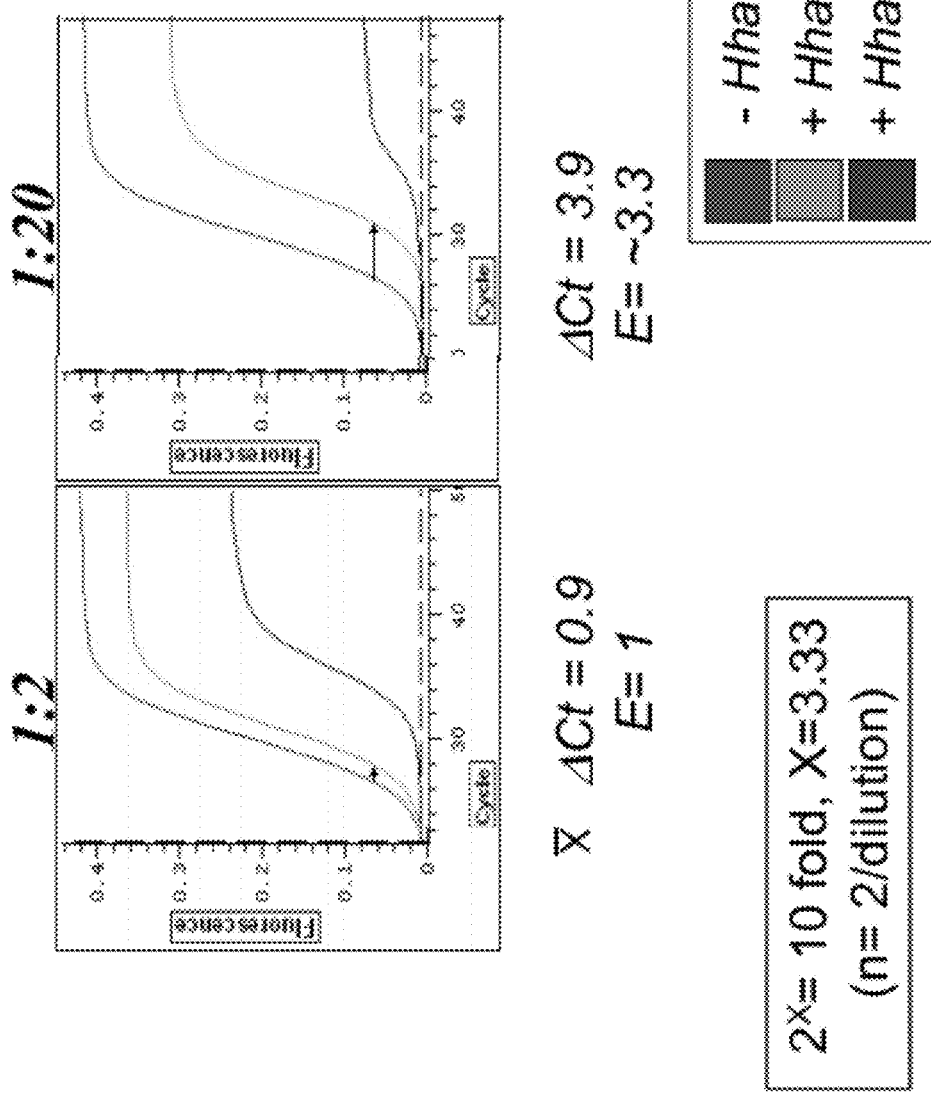

A "fragment" of DNA refers to an intact DNA molecule of variable size, which can be an entire chromosome or smaller segments thereof "Methylation" refers to methylation at positions $C^5$ or $N^4$ of cytosine, the $N^6$ position of adenosine or other types of nucleic acid methylation.

A "methylation-dependent restriction enzyme" refers to a restriction enzyme that cleaves at or near a methylated recognition sequence, but does not cleave at or near the same sequence when the recognition sequence is not methylated. Methylation-dependent restriction enzymes can recognize, for example, specific sequences comprising a methylated-cytosine or a methylated-adenosine. Methylation-dependent restriction enzymes include those that cut at a methylated recognition sequence (e.g., DpnI) and enzymes that cut at a sequence that is not at the recognition sequence (e.g., McrBC). For example, McrBC requires two half-sites. Each half-site must be a purine followed by 5-methyl-cytosine (R5mC) and the two half-sites must be no closer than 20 base pairs and no farther than 4000 base pairs away from each other (N20-4000). McrBC generally cuts close to one half-site or the other, but cleavage positions are typically distributed over several base pairs approximately 32 base pairs from the methylated base. Exemplary methylation-dependent restriction enzymes include, e.g., McrBC (see, e.g., U.S. Pat. No. 5,405,760), McrA, MrrA, and Dpn I. One of skill in the art will appreciate that homologs and orthologs of the restriction enzymes described herein are also suitable for use in the present invention.

A "methylation insensitive restriction enzyme" refers to a restriction enzyme that cuts DNA regardless of the methylation state of the base of interest (A or C) at or near the recognition sequence.

A "methylation sensing restriction enzyme" refers to a restriction enzyme whose activity changes in response to the methylation of its recognition sequence.

A "methylation-sensitive restriction enzyme" refers to a restriction enzyme (e.g., PstI) that cleaves at or in proximity to an unmethylated recognition sequence but does not cleave at or in proximity to the same sequence when the recognition sequence is methylated. Exemplary 5'-methyl cytosine sensitive restriction enzymes include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, or Zra I. See e.g., McClelland, M. et al, *Nucleic Acids Res.* 22(17):3640-59 (1994) and http://rebase.neb.com. Exemplary methyl adenosine sensitive restriction enzymes include, e.g., MboI.

As used herein, a "recognition sequence" refers only to a primary nucleic acid sequence and does not reflect the methylation status of the sequence.

The "methylation density" refers to the number of methylated residues in a given locus of DNA divided by the total number of nucleotides in the same DNA sequence that are capable of being methylated. Methylation density may be determined for methylated-cytosines or methylated-adenosines.

Cleaving DNA "under conditions that allow for at least some copies of potential restriction enzyme cleavage sites in the locus to remain uncleaved" refers to any combination of reaction conditions, restriction enzyme and enzyme concentration and/or DNA resulting in at least some of the DNA comprising a potential restriction enzyme cleavage site to remain uncut. For example, a partial digestion of the DNA (e.g., by limiting the amount of enzyme or the amount of time of the digestion) allows some potential restriction enzyme cleavage sites in the locus to remain uncut. Alternatively, a complete digestion using a restriction enzyme such as McrBC will result in some potential restriction enzyme cleavage sites in the locus to remain uncut because the enzyme does not always cut between the two recognition half sites, thereby leaving at least some uncleaved copies of a locus in a population of sequences wherein the locus is defined by the two recognition half-sites. A "potential restriction enzyme cleavage site" refers to a sequence that a restriction enzyme is capable of cleaving (i.e., comprising the appropriate nucleotide sequence and methylation status) when it recognizes the enzymes recognition sequence, which may be the same or different from the cleavage site.

"Amplifying" DNA refers to any chemical, including enzymatic, reaction that results in an increased number of copies of a template nucleic acid sequence. Amplification reactions include polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7):1691-6 (1992); Walker *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)); branched DNA signal amplification (bDNA) (see, e.g., Iqbal et al., *Mol. Cell Probes* 13(4):315-320 (1999)); and linear amplification.

A "partial digestion" of DNA as used herein refers to contacting DNA with a restriction enzyme under appropriate reaction conditions such that the restriction enzyme cleaves some (e.g., less than about 10%, 20%, 30%, 40%, 50%, 60%, 70%, 80%, or 90%) but not all of possible cleavage sites for that particular restriction enzyme in the DNA. A partial digestion of the sequence can be achieved, e.g., by contacting DNA with an active restriction enzyme for a shorter period of time than is necessary to achieve a complete digestion and then terminating the reaction, or under other altered reaction conditions that allow for the desired amount of partial digestion. "Possible sites" are generally enzyme recognition sequences, but also include situations where an enzyme cleaves at a sequence other than the recognition sequence (e.g., McrBC).

A "complete digestion" of DNA as used herein refers to contacting DNA with a restriction enzyme for sufficient time and under appropriate conditions to allow for cleavage of at least 95%, and typically at least 99%, or all of the restriction enzyme recognition sequences for the particular restriction enzyme. Conditions, including the time, buffers and other reagents necessary for complete digestions are typically provided by manufacturers of restriction enzymes. Those of skill in the art will recognize that the quality of the DNA sample may prevent complete digestion.

"Isoschizomers" refer to restriction enzymes that recognize the same nucleotide sequence. As used in this definition, the "same nucleotide sequence" is not intended to differentiate between methylated and unmethylated sequences. Thus, an "isoschizomeric partner" of a methylation-dependent or methylation-sensitive restriction enzyme is a restriction enzyme that recognizes the same recognition sequence as the methylation-dependent or methylation-sensitive restriction enzyme regardless of whether the recognition sequence is methylated.

"An agent that modifies unmethylated cytosine" refers to any agent that alters the chemical composition of unmethylated cytosine but does not change the chemical composition of methylated cytosine. An example of such an agent is sodium bisulfite.

"Primers that distinguish between methylated and unmethylated DNA" refers to oligonucleotides that:
  (i) hybridize (e.g., are at least partially complementary) to a sequence that represents a methylated DNA sequence after bisulfite conversion, but do not hybridize to a sequence representing the identical unmethylated sequence after bisulfite conversion; or
  (ii) hybridize to a sequence that represents an unmethylated DNA sequence after bisulfite conversion, but do not hybridize to a sequence representing the identical methylated sequence after bisulfite conversion.

As described herein, primers that distinguish between methylated and unmethylated sequences are generally designed to hybridize to a sequence that would occur if the DNA was treated with an agent (such as sodium bisulfite) that modifies unmethylated nucleotides but not methylated nucleotides or vice versa. For example, when sodium bisulfite is contacted to DNA, unmethylated cytosine is converted to uracil, while methylated cytosine is not modified. Since uracil forms complements with adenine, a primer that binds to the unmethylated sequence would contain adenines at locations, where the adenines would form complements with the modified cytosines (i.e., uracils). Similarly, if a primer that hybridized to sequences containing methylated cytosines was desired, the primer would contain guanosines, where it would form complements with the methylated cytosines. Thus, sequences that "represent" methylated or unmethylated DNA include DNA that result from sodium bisulfite treatment of the DNA.

A "locus" as used herein refers to a target sequence within a population of nucleic acids (e.g., a genome). If a single copy of the target sequence is present in the genome, then "locus" will refer to a single locus. If multiple copies of the target sequence are present in the genome, then "locus" will refer to all loci that contain the target sequence in the genome.

DETAILED DESCRIPTION OF THE INVENTION

I. Introduction

The present invention provides rapid and efficient methods for determining the presence of methylation and the methylation density in regions of genomic DNA. Determination of alterations in methylation density can be useful for providing diagnoses and prognoses for various diseases, including various cancers. While the methods of the invention also provide for the detection of specific methylation events, the present methods are particularly notable because they are not limited by a prediction or expectation that the methylation state of a particular nucleotide is determinative of a phenotype. In cases where the density of methylation (i.e., the quantity of nucleotides that are methylated in a particular length of a nucleic acid sequence), rather than the presence or absence of a particular methylated nucleotide, modulates gene expression, and where the methylation density of a locus reflects disease progression along a continuum, the present methods are particularly helpful.

II. Quantifying the Relative Amount of Methylation in Genomic DNA

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. As discussed below, the control value can represent a known or predicted number of methylated nucleotides. Alternatively, the control value can represent the quantity of intact or cut DNA from the same locus in another (e.g., normal, non-diseased) cell or a second locus.

As discussed in detail below, by using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus may be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample.

A. Digestion with Restriction Enzymes

Either partial or complete restriction enzyme digestions can be used to provide information regarding methylation density within a particular DNA locus.

i. Complete Digestion

When a DNA sample comprising a locus of interest is completely digested with a methylation sensing restriction enzyme, the information provided includes the presence or absence of methylation at recognition sequences of the restriction enzyme. The presence of intact DNA in a locus comprising the cut site of the restriction enzyme indicates that the appropriate methylation state of the recognition site necessary for cleavage by the methylation-sensitive or methylation-dependent restriction enzyme was not present at or near the locus, depending on the restriction enzyme.

The amount of intact test DNA can be compared to a control representing an equal amount of DNA from the sample that was not contacted with the restriction enzyme. Alternatively, the amount of intact DNA at a locus can be compared to similarly-treated intact DNA comprising a second locus or compared to the same locus in DNA isolated from another cell when all DNA samples are treated similarly. In another alternative, the amount of intact DNA at a locus can be compared to similarly-treated DNA having a known or expected number of methylated and monitorable restriction sites and comparable in size. Those of skill in the art will appreciate that other controls are also possible. Thus, by detecting the amount of intact DNA at the locus following restriction enzyme digestion, the relative number of methylated copies compared to the total number of copies of the locus is determined.

Use of restriction enzymes that have a variable cleavage pattern near the recognition sequence (e.g., McrBC) provides a special case for complete digestions of DNA. In this case, even if the locus contains a recognition sequence in the appropriate methylation state, some of the fragments containing a methylated locus will remain intact because cleavage of the DNA will occur outside the locus according to a function of probability. Therefore, a complete digestion with McrBC behaves similarly to a partial digestion with a methylation sensing restriction enzyme (which cuts at its recognition site) with respect to the number of intact alleles.

Figure 7:
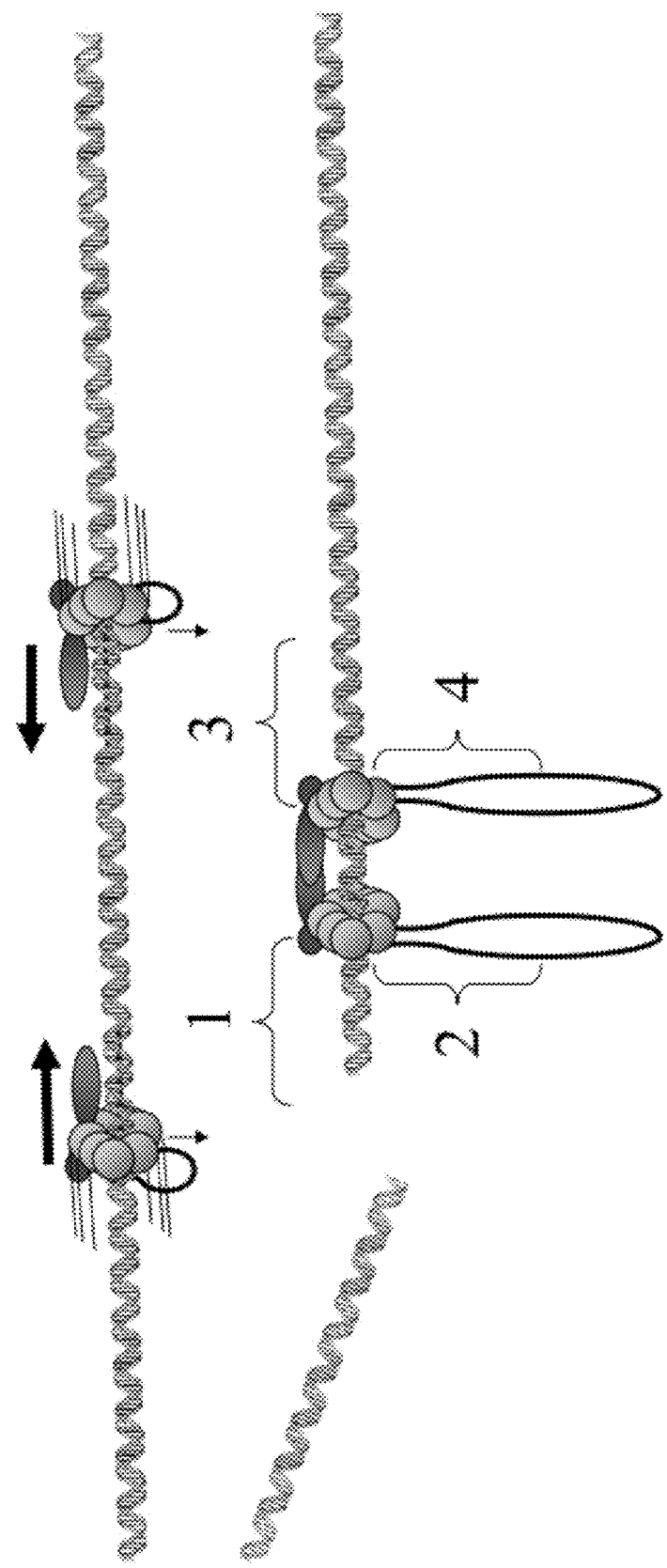
FIG. 7 illustrates McrBC DNA restriction.

The mechanism of McrBC DNA cutting occurs as follows. An eight subunit complex of McrB binds to each of two recognition half sites (purine-methylC represented as (A or G)mC). See FIG. 7. These complexes then recruit one McrC subunit to their respective half sites and start to translocate along the DNA mediated by GTP hydrolysis. When two McrBC bound complexes contact each other, a double-complex is formed and restriction occurs. Cutting will generally not occur if the two half sites are closer than 20 bp and restriction resulting from half sites as far as 4 kb from one another have been observed, though are rare. Restriction may occur ~32 bp to the left or right of either bound half site, giving four possible cut site locations: ~32 bp 5' of the first half site, ~32 bp 3' of the first half site, ~32 bp 5' of the second half site, and ~32 bp 3' of the second half site. Therefore, it is possible for two half sites to exist within a locus defined by PCR primers and for cleavage to occur outside of the locus. It is also possible for two half sites to exist outside of the locus and for a cut to occur within the locus. It is also possible for one site to exist in the locus and for another to exist outside of the locus and for a cut to occur either within or outside of the locus. Thus, the more methylated half sites that are "in the vicinity" of the locus (whether literally between the amplification primers or in neighboring flanking sequence), the more likely a cut will be observed within the locus for a given concentration of McrBC. Accordingly, the number of copies of a methylated locus that are cleaved by McrBC in a complete or partial digestion will be proportional to the density of methylated nucleotides.

ii. Partial Digestions

The amount of cleavage with a methylation sensitive or methylation-dependent restriction enzyme in a partial (i.e., incomplete) digestion reflects the average methylation density within the locus of DNA in the sample. For instance, when a locus has a higher methylation density than a control, then a partial digestion using a methylation-dependent restriction enzyme will cleave copies of the locus more frequently. Similarly, when a locus has a lower methylation density than a control, then a partial digestion using a methylation-dependent restriction enzyme will cleave copies of the locus less frequently within the locus because fewer recognition sites are present. Alternatively, when a methylation sensitive restriction enzyme is used, fewer copies of a locus with a higher methylated density are cleaved less, and thus more intact DNA strands containing the locus are present. In each of these cases, the digestion of DNA sample in question is compared to a control value such as those discussed above for complete digestions. Alternatively, the quantity of intact DNA after digestion can be compared to a second sample to determine relative methylation density between the samples.

It can be useful to test a variety of conditions (e.g., time of restriction, enzyme concentration, different buffers or other conditions that affect restriction) to identify the optimum set of conditions to resolve subtle or gross differences in methylation density among two or more samples. The conditions may be determined for each sample analyzed or may be determined initially and then the same conditions may be applied to a number of different samples.

iii. DNA Samples

DNA can be obtained from any biological sample can be used, e.g., from cells, tissues, secretions, and/or fluids from an organism (e.g., an animal, plant, fungus, or prokaryote). The samples may be fresh, frozen, preserved in fixative (e.g., alcohol, formaldehyde, paraffin, or PreServeCyte™) or diluted in a buffer. Biological samples include, e.g., skin, blood or a fraction thereof, tissues, biopsies (from e.g., lung, colon, breast, prostate, cervix, liver, kidney, brain, stomach, esophagus, uterus, testicle, skin, hair, bone, kidney, heart, gall bladder, bladder, and the like), body fluids and secretions (e.g., blood, urine, mucus, sputum, saliva, cervical smear specimens, marrow, feces, sweat, condensed breath, and the like). Biological samples also include, leaves, stems, roots, seeds, petals, pollen, spore, mushroom caps, and sap.

The above-described digestions can be used to analyze a sample of DNA where all copies of a genomic DNA locus have an identical methylation pattern. In other embodiments, the DNA sample is a mixture of DNA comprising alleles of a DNA locus in which some alleles are more methylated than others. In some embodiments, a DNA sample contains DNA from two or more different cell types, wherein each cell type has a different methylation density at a particular locus. For example, at some loci, neoplastic cells have different methylation densities compared to normal cells. If a tissue, body fluid, or secretion contains DNA from both normal and neoplastic cells, then the DNA sample from the tissue, body fluid, or secretion will comprise a heterogeneous mixture of differentially methylated alleles. In this case, at a given locus, one set of alleles within the DNA (e.g., those derived from neoplastic cells in the sample) will have a different methylation density than the other set of alleles (e.g., those derived from normal cells).

In mixed samples (e.g., in biopsies comprising healthy and diseased cell), it may be helpful to focus results on one population of nucleic acids in the sample (e.g., from diseased cells) rather than to determine the average methylation density across DNA from all cells in the sample. In some embodiments in which a first population of DNA in the sample has low or no methylation and the second population of DNA in the sample has more methylation than the first population, density in the second population can be determined by cleaving the sample with one or more methylation-sensitive restriction enzymes (generally cut to "completion"), thereby degrading the first population while leaving the second population substantially intact. Thus, the sample may also be contacted with a methylation-dependent restriction enzyme (using McrBC and/or any methylation-dependent restriction enzyme under partial digestion conditions) and the remaining intact DNA may be amplified, thereby determining the methylation density in the second population. The methylation density of the first population may be similarly determined by contacting the sample with one or more methylation-dependent restriction enzymes (generally cut to "completion") and contacting the sample with a methylation sensitive under partial digestion conditions. In this case, the amplified DNA will represent the methylation density of the first population.

B. Amplification to Detect Intact DNA

The presence and quantity of DNA cleaved by the restriction enzymes can be determined by amplifying the locus following digestion. By using amplification techniques (e.g., the polymerase chain reaction (PCR)) that require the presence of an intact DNA strand for amplification, the presence and amount of remaining uncut DNA can be determined. For example, PCR reactions can be designed in which the amplification primers flank a particular locus of interest. Amplification occurs when the locus comprising the two primers remains intact following a restriction digestion. If the amount of total and intact DNA is known, the amount of cleaved DNA can be determined. Since cleavage of the DNA depends on the methylation state of the DNA, the intact and cleaved DNA represents different methylation states.

Amplification of a DNA locus using reactions is well known (see U.S. Pat. Nos. 4,683,195 and 4,683,202; *PCR Protocols: A Guide to Methods and Applications* (Innis et al., eds, 1990)). Typically, PCR is used to amplify DNA templates. However, alternative methods of amplification have been described and can also be employed, as long as the alternative methods amplify intact DNA to a greater extent than the methods amplify cleaved DNA.

DNA amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology* 3:1008-1012 (1985)), allele-specific oligonucleotide (ASO) probe analysis (Conner, et al., *Proc. Natl. Acad. Sci. USA* 80:278 (1983)), oligonucleotide ligation assays (OLAs) (Landegren, et al., *Science* 241:1077, (1988)), and the like. Molecular techniques for DNA analysis have been reviewed (Landegren, et al., *Science* 242:229-237 (1988)).

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications may be monitored in "real time."

In general, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487,972; Holland et al., *Proc. Natl. Acad. Sci. USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer (*Nature Biotech.* 14:303-309 (1996)), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in the hairpin (closed) conformation, the fluorescence of the donor fluorophore is quenched. When employed in PCR, the molecular beacon probe, which hybridizes to one of the strands of the PCR product, is in the open conformation and fluorescence is detected, and the probes that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acid are also known. For example, some methodologies employ one or more probe oligonucleotides that are structured such that a change in fluorescence is generated when the oligonucleotide(s) is hybridized to a target nucleic acid. For example, one such method involves a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™)

In other embodiments, intercalating agents that produce a signal when intercalated in double stranded DNA may be used. Exemplary agents include SYBR GREEN™ and SYBR GOLD™. Since these agents are not template-specific, it is assumed that the signal is generated based on template-specific amplification. This can be confirmed by monitoring signal as a function of temperature because melting point of template sequences will generally be much higher than, for example, primer-dimers, etc.

C. Hybrid Capture

In some embodiments, nucleic acid hybrid capture assays can be used to detect the presence and quantity of DNA cleaved by the restriction enzymes. This method can be used with or without previously amplifying the DNA. Following the restriction digests, RNA probes which specifically hybridize to DNA sequences of interest are combined with the DNA to form RNA:DNA hybrids. Antibodies that bind to RNA:DNA hybrids are then used to detect the presence of the hybrids and therefore, the presence and amount of uncut DNA.

DNA fragments that are restricted in a window of sequence that is complimentary to the RNA probe hybridize less efficiently to the RNA probe than do DNA fragments that remain intact in the window of sequence being monitored. The amount of hybridization allows one to quantify intact DNA, and the quantity of DNA methylation can be inferred directly from the quantity of intact DNA from different restriction enzyme treatments (i.e., methylation-sensitive and/or methylation-dependent restriction enzyme treatments).

Methods of detecting RNA:DNA hybrids using antibodies are known in the art and are described in, e.g., Van Der Pol et al., *J. Clin. Microbiol.* 40(10): 3558 (2002); Federschneider et al., *Am. J. Obstet. Gynecol.* 191(3):757 (2004); Pretet et al., *J. Clin. Virol.* 31(2):140-7 (2004); Giovannelli et al., *J. Clin. Microbiol.* 42(8):3861 (2004); Masumoto et al., *Gynecol. Oncol.* 94(2):509-14 (2004); Nonogaki et al., *Acta Cytol.* 48(4):514 (2004); Negri et al., *Am. J. Clin. Pathol.* 122(1):90 (2004); Sarian et al., *Gynecol. Oncol.* 94(1):181 (2004); Oliveira et al., *Diagn. Cytopathol.* 31(1):19 (2004); Rowe et al., *Diagn. Cytopathol.* 30(6):426 (2004); Clavel et al., *Br. J. Cancer* 90(9):1803-8 (2004); Schiller et al., *Am. J. Clin. Pathol.* 121(4):537 (2004); Arbyn et al., *J. Natl. Cancer Inst.*

96(4):280 (2004); Syrjanen et al., *J. Clin. Microbiol.* 2004 February; 42(2):505 (2004); Lin et al., *J. Clin. Microbiol.* 42(1):366 (2004); Guyot et al., *BMC Infect. Dis.* 25; 3(1):23 (2003); Kim et al., *Gynecol. Oncol.* 89(2):210-7 (2003); Negri et al., *Am J Surg Pathol.* 27(2):187 (2003); Vince et al., *J. Clin. Virol.* Suppl 3:S109 (2002); Poljak et al., *J. Clin. Virol.* Suppl 3:S89 (2002). In some cases, the antibodies are labeled with a detectable label (e.g., an enzymatic label, an isotope, or a fluorescent label) to facilitate detection. Alternatively, the antibody:nucleic acid complex may be further contacted with a secondary antibody labeled with a detectable label. For a review of suitable immunological and immunoassay procedures, see, e.g., Harlow & Lane, ANTIBODIES, A LABORATORY MANUAL, Cold Spring Harbor Publication, New York (1988); *Basic and Clinical Immunology* (Stites & Terr eds., $7^{th}$ ed. 1991); U.S. Pat. Nos. 4,366,241; 4,376,110; 4,517,288; and 4,837,168); Methods in Cell Biology: Antibodies in Cell Biology, volume 37 (Asai, ed. 1993).

Monoclonal, polyclonal antibodies, or mixtures thereof may be used to bind the RNA:DNA hybrids. Detection of RNA:DNA hybrids using monoclonal antibodies is described in, e.g., U.S. Pat. Nos. 4,732,847 and 4,833,084. Detection of RNA:DNA hybrids using polyclonal antibodies is described in, e.g., U.S. Pat. No. 6,686,151. The polyclonal or monoclonal antibodies may be generated with specific binding properties. For example, monoclonal or polyclonal antibodies that specifically bind to shorter (e.g., less than 20 base pairs) or longer (e.g., more than 100 base pairs) RNA:DNA hybrids may be generated. In addition, monoclonal or polyclonal antibodies may be produced that are either more or less sensitive to mismatches within the RNA:DNA hybrid.

Methods of producing polyclonal and monoclonal antibodies that react specifically with RNA:DNA hybrids are known to those of skill in the art. For example, preparation of polyclonal and monoclonal antibodies by immunizing suitable laboratory animals (e.g., chickens, mice, rabbits, rats, goats, horses, and the like) with an appropriate immunogen (e.g., an RNA:DNA hybrid). Such methods are described in, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495497 (1975).

Antibodies can also be recombinantly produced. Antibody preparation by selection of antibodies from libraries of nucleic acids encoding recombinant antibodies packaged in phage or similar vectors is described in, e.g., Huse et al., *Science* 246:1275-1281 (1989) and Ward et al., *Nature* 341:544-546 (1989). In addition, antibodies can be produced recombinantly using methods known in the art and described in, e.g., Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

D. Generation of Control Values

Control values can represent either external values (e.g., the number of intact loci in a second DNA sample with a known or expected number of methylated nucleotides or methylated restriction enzyme recognition sequences) or internal values (e.g., a second locus in the same DNA sample or the same locus in a second DNA sample). While helpful, it is not necessary to know how many nucleotides (i.e., the absolute value) in the control are methylated. For example, for loci in which methylation results in a disease state, knowledge that the locus is more methylated than it is in normal cells can indicate that the subject from which the sample was obtained may have the disease or be in the early stages of developing disease.

In cases where the same DNA sample includes a control locus, multiplex amplification, e.g., multiplex PCR can be used to analyze two more loci (e.g., at least one target locus and at least one control locus).

DNA samples can vary by two parameters with respect to methylation: (i) the percentage of total copies in a population that have any methylation at a specific locus, and (ii) for copies with any DNA methylation, the average methylation density among the copies. It is ideal, though not required, to use control DNAs that evaluate both of these parameters in a test sample.

Control DNAs with known methylated cytosines are produced using any number of DNA methylates, each of which can have a different target methylation recognition sequence. This procedure can create a population of DNA fragments that vary with respect to the methylation density (i.e., the number of methylated cytosines per allele). Partial methylase reactions can also be used, e.g., to produce a normally distributed population with a mode at the average methylation density for the population. In some embodiments, the mode can be adjusted for a given population as a function of the completeness of the methylase reaction. Control DNAs can also be synthesized with methylated and unmethylated DNA bases.

In some cases, a DNA target with a known sequence is used. A desired control DNA can be produced by selecting the best combination of methylases and restriction enzymes for the analysis. First, a map of sites that can be methylated by each available methylase is generated. Second, a restriction map of the locus is also produced. Third, methylases are selected and are used to in vitro methylate the control DNA sample to bring about a desired methylation pattern, which is designed to perform optimally in combination with the restriction enzymes used in the methylation analysis of the test DNA and control DNA samples. For example, M.HhaI methylates the site (G*CGC) and McrBC recognizes two half sites with the motif (RpC). Therefore, each methylated M.HhaI site in the control sequence is recognized by McrBC.

Similarly, a population of molecules may be then treated with a DNA methylase (e.g., M.SssI) in the presence of magnesium to result in a desired methylation density. If the reaction is allowed to run to completion, nearly all of the sites that can be methylated will be methylated, resulting in a high and homogeneous methylation density. If the reaction is limited in its course, a lower average methylation density (or partial methylation) will result (i.e., all possible sites are not methylated due to timing of reaction and/or concentration of enzyme). In this way, the desired average methylation density of the control DNA can be produced. The methylated control DNA can be precisely characterized by determining the number of methylated cytosines through bisulfite sequencing. Alternatively, the methylation control DNA can be precisely characterized by determining the number of methylated cytosines through a comparison to other known control DNAs as described herein.

For more precise prediction of methylation densities, it may be useful to generate a control set of DNA that can conveniently serve as a standard curve, where each sample in the control set has a different methylation density, either known or unknown. By cutting the multiple samples with a methylation-dependent restriction enzyme or a methylation-sensitive restriction enzyme under conditions that allow for at least some copies of potential restriction enzyme cleavage sites in the locus to remain uncleaved and subsequently amplifying the remaining intact copies of a locus, a standard curve of the amount of intact copies (e.g., represented by Ct values) can be generated, thereby correlating the amount of intact DNA to different methylation densities. The standard curve can then be used to determine the methylation density of a test DNA sample by interpolating the amount of intact DNA in the sample following restriction and amplification as described herein.

E. Methylation State-Specific Amplification

In some embodiments, methylation-specific PCR can be employed to monitor the methylation state of specific nucleotides in a DNA locus. In these embodiments, following or preceding digestion with the restriction enzyme, the DNA is combined with an agent that modifies unmethylated cytosines. For example, sodium bisulfite is added to the DNA, thereby converting unmethylated cytosines to uracil, leaving the methylated cytosines intact. One or more primers are designed to distinguish between the methylated and unmethylated sequences that have been treated with sodium bisulfite. For example, primers complementary to the bisulfite-treated methylated sequence will contain gua-nosines, which are complementary to endogenous cytosines. Primers complementary to the bisulfite-treated unmethylated sequence will contain adenosine, which are complementary to the uracil, the conversion product of unmethylated cytosine. Preferably, nucleotides that distinguish between the converted methylated and unmethylated sequences will be at or near the 3' end of the primers. Variations of methods using sodium bisulfite-based PCR are described in, e.g., Herman et al., *Proc. Natl. Acad. Sci. USA* 93:9821-9826 (1996); U.S. Pat. Nos. 5,786,146 and 6,200,756.

F. Detection of Methylation Associated with Disease

Amplification primers can be designed to amplify loci associated with a particular phenotype or disease. Detection of altered methylation profiles at loci where such alterations are associated with disease can be used to provide diagnoses or prognoses of disease. See, e.g., Table 1. See, also, Costello and Plass, *J Med Genet* 38:285-303 (2001) and Jones and Baylin, *Nature. Rev* 3:415-428 (2002).

TABLE 1

Examples of Genes Exhibiting Hypermethylation in Cancer

| Gene | Effect of loss of function in tumor development | Tumor types |
| --- | --- | --- |
| RB | Loss of cell-cycle control | Retinoblastoma |
| MLH1 | Increased mutation rate, drug resistance | Colon, ovarian, endometrial, gastric |
| BRCA1 | Genomic instability | Breast, ovarian |
| E-CAD | Increased cell motility | Breast, gastric, lung, prostate, colon, leukemia |
| APC | Aberrant cell transduction | Breast, lung, colon, gastric, esophageal, pancreatic, hepatocellular |
| p16 | Loss of cell-cycle control | Most tumor types |
| VHL | Altered protein degradation | Clear-cell renal cell carcinoma |
| p73 | Loss of cell-cycle control | Leukemia, lymphoma, ovarian |
| RASSF1A | Aberrant cell transduction | Lung, breast, ovarian, kidney, nasopharyngeal |
| p15 | Loss of cell-cycle control | Leukemia, lymphoma, gastric, squamous cell carcinoma, hepatocellular |
| GSTP1 | Increased DNA damage | Prostate |
| DAPK | Reduced apoptosis | Lymphoma, lung |
| MGMT | Increased mutation rate | Colon, lung, brain, esophageal, gastric |
| P14ARF | Loss of cell cycle control | Melanoma, non-melanoma skin cancer, pancreatic, breast, head and neck, lung, mesothelioma, neurofinromatosis, colon, soft tissue sarcoma., bladder, Hodgkin's, Ewing's sarcoma, Wilm's tumor, osteosarcoma, rhabdomyosarcoma |
| ATM | Defective DNA repair | Leukemia, lymphoma |
| CDKN2B | Loss of cell cycle control | Breast, ovarian, prostate |
| FHIT | Defective DNA repair | Lung, pancreas, stomach, kidney, cervix, breast |
| MSH2 | Defective DNA repair | Colon |
| NF1/2 | Loss of cell cycle control | Neurofibroma |
| PTCH | Loss of cell cycle control | Skin, basal and squamous cell carcinomas, brain |
| PTEN | Loss of cell cycle control | Breast, thyroid, skin, head and neck, endometrial |
| SMAD4 | Loss of cell cycle control | Pancreas, colon |
| SMARCA3/B1 | Loss of cell cycle control | Colon |
| STK11 | Loss of cell cycle control | Melanoma, gastrointestinal |
| TIMP3 | Disruption of cellular matrix | Uterus, breast, colon, brain, kidney |
| TP53 | Loss of cell cycle control; reduced apoptosis | Colon, prostate, breast, gall bladder, bile duct, |
| BCL2 | Loss of cell cycle control; reduced apoptosis | Lymphoma, breast |
| OBCAM | Loss of cell cycle control | Ovarian |
| GATA4 | Transcriptional silencing of downstream genes | Colorectal, gastric, ovary |

TABLE 1-continued

Examples of Genes Exhibiting Hypermethylation in Cancer

| Gene | Effect of loss of function in tumor development | Tumor types |
|------|--------------------------------------------------|-------------|
| GATA5 | Transcriptional silencing of downstream genes | Colorectal, gastric, ovary |
| HIC1 | Loss of cell cycle control | Epithelium, lymphoma, sarcoma |

Abbreviations:
APC, adenomatous polyposis coli;
BRCA1, breast cancer 1;
DAPK, death-associated protein kinase;
E-cad, epithelial cadherin;
GSTP1 glutathione S-transferase π1;
MLH1, MutL homologue 1,
MGMT, O(6)-methylguanine-DNA methyltransferase;
p15, $p15^{INK4b}$;
p16, $p16^{INK4}$;
p73, p73;
Rb, retinoblastoma;
RASSF1a, Ras association domain family 1A;
VHL, von Hippel-Lindau;
ATM, ataxia telangiectasia mutated;
CDKN2, cyclin dependent kinase inhibitor;
FHIT, fragile histidine triad;
MSH2, mutS homologue 2;
NF½, neurofibromin ½;
PTCH, patched homologue;
PTEN, phosphatase and tensin homologue;
SMAD4, mothers against decapentaplegic homologue 4;
SMARCA3/B1, SWI/SNF-related, matrix-associated, actin-dependent regulator of chromatin, subfamily A, member 3/subfamily B, member 1;
STK11, serine/threonine kinase 11;
TIMP3, tissue inhibitor of metalloproteinase 3;
Bcl-2m B-call CLL/Lymphoma 2;
OBCAM, opoid-binding cell adhesion molecule;
GATA, globin transcription factor;
HIC1, hypermethylated in cancer.

For example, methylation of the p16 locus is associated with pancreatic cancer. See, e.g., Schutte et al., *Cancer Res.* 57:3126-3131 (1997). Methylation changes at the insulin-like growth factor II/H19 locus in kidney are associated with Wilms tumorigenesis. See, e.g., Okamoto et al., *Proc. Natl. Acad. Sci. USA* 94:5367-5371 (1997). The association of alteration of methylation in the p15, E-cadherin and von Hippel-Lindau loci are also associated with cancers. See, e.g., Herman et al., *Proc. Natl. Acad. Sci. USA* 93:9821-9826 (1997). The methylation state of GSTP1 is associated with prostate cancer. See, e.g., U.S. Pat. No. 5,552,277.

Genomic DNA samples can be obtained by any means known in the art. In cases where a particular phenotype or disease is to be detected, DNA samples should be prepared from a tissue of interest, or as appropriate, from blood. For example, DNA can be prepared from biopsy tissue to detect the methylation state of a particular locus associated with cancer. The nucleic acid-containing specimen used for detection of methylated loci (see, e.g., Ausubel et al., *Current Protocols in Molecular Biology* (1995 supplement)) may be from any source and may be extracted by a variety of techniques such as those described by Ausubel et al., *Current Protocols in Molecular Biology* (1995) or Sambrook et al., *Molecular Cloning, A Laboratory Manual* (3rd ed. 2001). Exemplary tissues include, e.g., brain, colon, urogenital, hematopoietic, thymus, testis, ovarian, uterine, prostate, breast, colon, lung and renal tissue.

Detection and identification of loci of altered methylation (compared to normal cells) in DNA samples can indicate that at least some of the cells from which the sample was derived are diseased. Such diseases include but are not limited to, e.g., low grade astrocytoma, anaplastic astrocytoma, glioblastoma, medulloblastoma, colon cancer, liver cancer, lung cancer, renal cancer, leukemia (e.g., acute lymphocytic leukemia, chronic lymphocytic leukemia, acute myeloid leukemia, chronic myeloid leukemia), lymphoma, breast cancer, prostate cancer, cervical cancer, endometrial cancer, neuroblastoma, cancer of the oral cavity (e.g., tongue, mouth, pharynx), esophageal cancer, stomach cancer, cancer of the small intestine, rectal cancer, anal cancer, cancer of the anal canal and anorectum, cancer of the intrahepatic bile duct, gallbladder cancer, biliary cancer, pancreatic cancer, bone cancer, cancer of the joints, skin cancer (e.g., melanoma, non-epithelial cancer, basal cell carcinoma, squamous cell carcinoma), soft tissue cancers, uterine cancer, ovarian cancer, vulval cancer, vaginal cancer, urinary cancer, cancer of the ureter, cancer of the eye, head and neck cancer, non-Hodgkin lymphoma, Hodgkin lymphoma, multiple myeloma, brain cancer, cancer of the nervous system. Identification of altered methylation profiles is also useful for detection and diagnosis of loss of genomic imprinting, fragile X syndrome and X-chromosome inactivation.

If desired, multiplex DNA methods can be used to amplify multiple targets from the same sample. The additional targets can represent controls (e.g., from a locus of known methylation status) or additional loci associated with a phenotype or disease.

In some embodiments, the methods of the invention are used to identify new loci associated with a disease phenotype, such as cancer, or are used to validate such an association.

F. Exemplary Methods of Determining Relative Methylation at a Locus

As described above, a number of possibilities are available for determining the relative amount of methylation at a genetic locus of interest. For example, partial or complete digestions can be performed, methylation-sensitive or methylation-dependent restriction enzymes can be used, sodium bisulfite treatment can be employed, etc. Without intending to limit the invention to a particular series of steps, the following possibilities are further exemplified.

In some embodiments, a DNA sample is digested (partially or to completion) with McrBC or another methylation-dependent restriction enzyme and a locus is subsequently amplified using quantitative DNA amplification (e.g., PCR, rolling circle amplification, and other methods known to those skilled in the art). The resulting kinetic profiles of the amplification reactions are compared to those derived from a similarly treated control DNA sample. Kinetic profiles of amplification reactions can be obtained by numerous means known to those skilled in the art, which include fluorescence reaction monitoring of TaqMan™, molecular beacons, intercalating dye (e.g., Sybr Green™) incorporation, SCORPION™ probes, and others.

In some embodiments, the DNA sample is split into equal portions and one portion is treated with the methylation-dependent restriction enzyme and the other is not. The two portions are amplified and compared to determine the relative amount of methylation at the locus.

In some embodiments, the DNA sample can be split into equal portions, wherein each portion is submitted to a different amount of partial digestion with McrBC or another methylation-dependent restriction enzyme. The amount of intact locus in the various portions (e.g., as measured by quantitative DNA amplification) can be compared to a control population (either from the same sample representing uncut DNA or equivalent portions from another DNA sample). In cases where the equivalent portions are from a second DNA sample, the second sample can have an expected or known number of methylated nucleotides (or at least methylated restriction enzyme recognition sequences) or, alternatively, the number of methylated recognition sequences can be unknown. In the latter case, the control sample will often be from a sample of biological relevance, e.g., from a diseased or normal tissue, etc.

In some embodiments, the DNA sample is partially digested with one or more methylation-sensitive restriction enzymes and then amplified to identify intact loci. Controls in these cases are similar to those used for methylation-dependent restriction enzyme digestions described above. Untreated controls are undigested, and any treated control DNA samples are digested with methylation-sensitive restriction enzymes.

In some embodiments, a sample is separated into at least two portions. The first portion is digested with an enzyme from one of the three possible methylation-sensing classes of restriction enzymes (i.e., methylation sensitive, methylation insensitive, and methylation dependent). Each additional portion is digested with the isoschizomeric partner from a different methylation-sensing class from the enzyme used to digest the first portion. The intact loci are then amplified and quantified. The relative methylation at the locus can be determined by comparing the results obtained from any two of the reactions to each other, with or without comparison to an undigested portion. In the case where methylation insensitive enzymes are used, the portion typically undergoes a partial digestion.

In some embodiments, the DNA sample is treated with an agent that modifies unmethylated cytosine, but leaves methylated cytosine unmodified, e.g., sodium bisulfite. The sample is separated into equal portions, and one portion is treated with a methylation-dependent restriction enzyme (e.g., McrBC). Sodium bisulfite treatment does not modify McrBC recognition sites because sodium bisulfite modifies unmethylated cytosine and the recognition site of each McrBC hemisite is a purine base followed by a methylated cytosine. Samples from both cut and uncut portions are then amplified using at least one primer that distinguishes between methylated and unmethylated nucleotides. The amplified portions are then compared to determine relative methylation. Certain quantitative amplification technologies employ one or more detection probes that are distinct from the amplification primers. These detection probes can also be designed to discriminate between converted methylated and unmethylated DNA. In some embodiments, the detection probes are used in combination with a methylation-dependent restriction enzyme (e.g., McrBC). For example, the detection probes can be used to quantify methylation density within a locus by comparing the kinetic amplification profiles between a converted McrBC treated sample and a converted sample that was not treated with McrBC.

Alternatively, in some embodiments, the sample is divided into equal portions and one portion is digested (partially or completely) with a methylation-dependent restriction enzyme (e.g., McrBC). Both portions are then treated with sodium bisulfite and analyzed by quantitative amplification using a primer that distinguishes between converted methylated and unmethylated nucleotides. The amplification products are compared to each other as well as a standard to determine the relative methylation density.

In some embodiments, the DNA sample is divided into portions and one portion is treated with one or more methylation-sensitive restriction enzymes. The digested portion is then further subdivided and one subdivision is digested with a methylation-dependent restriction enzyme (e.g., McrBC). The various portions and subportions are then amplified and compared. Following digestion, the portions and subportions can optionally be treated with sodium bisulfite and amplified using at least one primer that distinguishes between methylated and unmethylated nucleotides.

Figure 13:
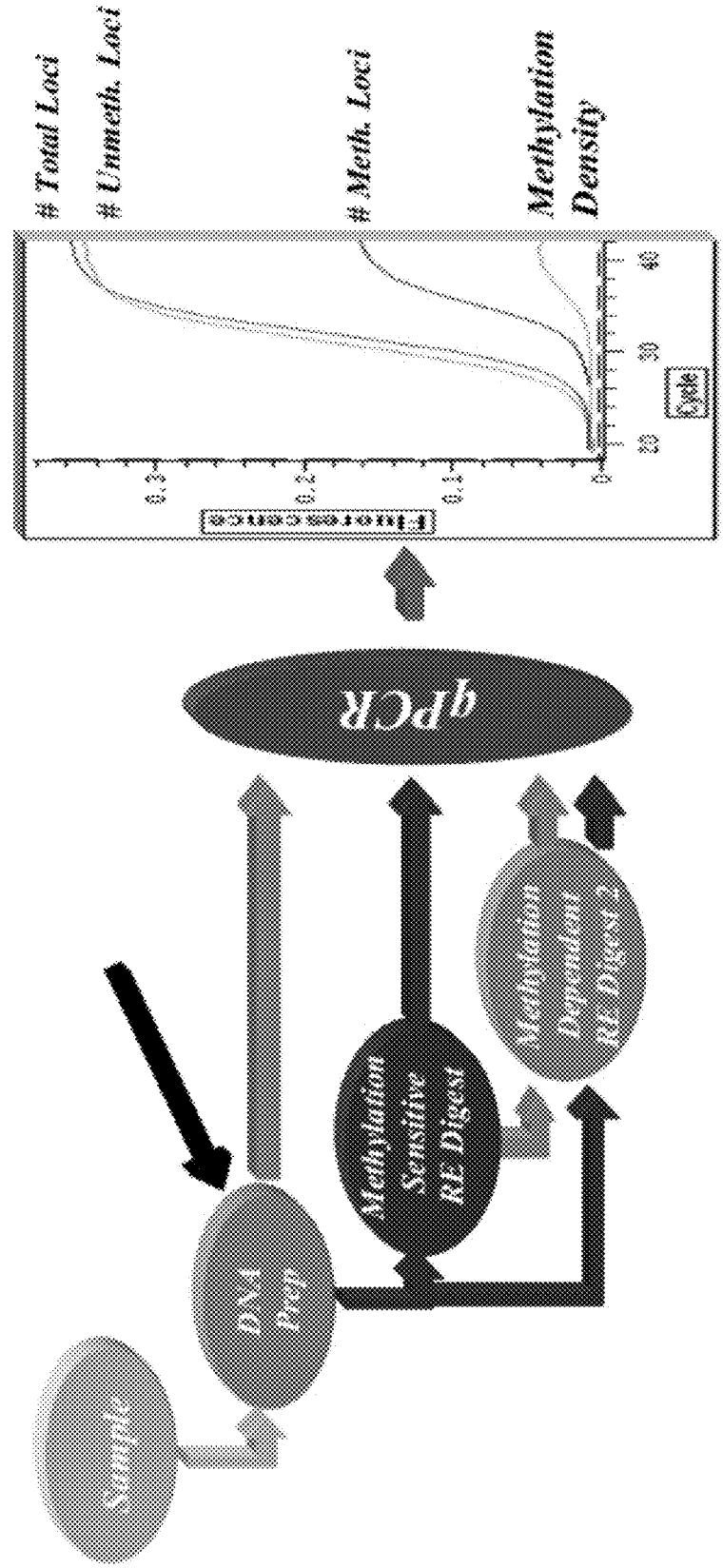
FIG. 13 illustrates comparison of different restriction enzyme digests to provide additional analysis of DNA methylation.

In some embodiments, the DNA sample is divided into four portions: a first portion is left untreated, a second portion is contacted with a methylation-sensitive restriction enzyme (wherein intact sequences are methylated), a third portion is contacted with a methylation-dependent restriction enzyme (wherein intact sequences are unmethylated), and a fourth portion is contacted with a methylation-sensitive restriction enzyme and a methylation-dependent restriction enzyme in which one of the restriction enzymes in the fourth portion is contacted to the sample under conditions that allow for at least some copies of potential restriction enzyme cleavage sites in the locus to remain uncleaved (e.g., under partial digest conditions and/or using McrBC). See, FIG. 13. If desired, a fifth portion of the sample can be analyzed following treatment with a methylation insensitive isoschizomer of a methylation-dependent or methylation-sensitive restriction enzyme used in another portion, thereby controlling for incomplete digestions and/or mutations at the restriction enzyme recognition sequence. In addition to digestion, the portions and subportions can optionally be treated with sodium bisulfite and amplified using at least one primer that distinguishes between methylated and unmethylated nucleotides.

III. Calculation of Methylation Density Based on Cycle Thresholds

As described above, cycle thresholds (Ct) are a useful measurement for determining the initial amount of DNA template in an amplification reaction. Accordingly, Ct values from samples treated with a methylation-dependent and/or methylation-sensitive restriction enzyme and amplified as described herein can be used to calculate methylation density at recognition sequences of the methylation-sensitive or methylation-dependent restriction enzymes used. A change in Ct value between one sample and a control value (which can represent the Ct value from a second sample) is predictive of relative methylation density. Because amplification in PCR theoretically doubles copies every cycle, $2^X$ approximates the number of copies in the amplification during exponential amplification, where X is the number of cycles. Thus $2^{Ct}$ is proportional to the amount of intact DNA at the initiation of amplification. The change of Ct (ΔCt) between two samples or between a sample and a control value (e.g., representing a Ct value from a control) represents the difference in initial starting template in the samples. Therefore, $2^{|\Delta Ct|}$ is proportional to the relative methylation density difference between a sample and a control or a second sample. For instance, as explained in Example 9, a difference of 1.46 in the Ct between two samples (each treated with a methylation-dependent restriction enzyme and subsequently amplified) indicates that one sample has at least 2.75 (i.e., $2^{(1.46)}$=2.75) times more potential methylated restriction sites within the locus than the other sample.

VI. Kits

The present invention also provides kits for performing the methods of the invention. For example, the kits of the invention can comprise, e.g., a methylation-dependent restriction enzyme or a methylation sensitive restriction enzyme, a control DNA molecule comprising a pre-determined number of methylated nucleotides, and one or two different control oligonucleotide primers that hybridize to the control DNA molecule. In some cases, the kits comprise a plurality of DNA molecules comprising different pre-determined numbers of methylated nucleotides to enable the user to compare amplification of a sample to several DNAs comprising a known number of methylated nucleotides.

The kits of the invention will often contain written instructions for using the kits. The kits can also comprise reagents sufficient to support the activity of the restriction enzyme. The kits can also include a thermostable DNA polymerase.

In some cases, the kits comprise one or two different target oligonucleotide primers that hybridize to a pre-determined region of human genomic DNA. For example, as described above, the primers can allow for amplification of loci associated with the development or prognosis of disease.

In some embodiments, the kits may comprise one or more detectably-labeled oligonucleotide probes to monitor amplification of target polynucleotides.

In some embodiments, the kits comprise at least one target oligonucleotide primer that distinguishes between modified unmethylated and methylated DNA in human genomic DNA. In these embodiments, the kits also typically include a fluorescent moiety that allows the kinetic profile of any amplification reaction to be acquired in real time.

In some embodiments, the kits comprise at least one target oligonucleotide primer that distinguishes between modified unmethylated and methylated DNA in human genomic DNA. In these embodiments, the kits will also typically include an agent that modifies unmethylated cytosine.

In some embodiments, the kits comprise an RNA probe, a binding agent (e.g., an antibody or an antibody mimetic) that specifically binds RNA:DNA complexes, detection reagents, and methylation sensitive and/or methylation dependent restriction enzymes.

EXAMPLES

Example 1

Constructing a DNA Methylation Standard Sample Set

A standard sample set is generated in numerous ways. For example, a methylase (e.g., M.SssI or other methylates such as MHhaI, M.AluI) is applied in vitro to a series of DNA samples to produce a standard set of DNAs known to have increasing methylation densities. This standard set is generated by first obtaining a sample of known sequence (e.g., the locus of interest). Next, the sample is divided into a series of samples and each sample in the series is treated with the chosen methylase in the presence of magnesium and in a manner that results in increasing methylation densities of the samples in the series.

A partial methylation reaction refers to contacting DNA with a cocktail of one or more methylases under appropriate reaction conditions such that the methylase modifies some (e.g., about 10%, 20%, 30%, 40%, 50%, 60%, 70%, 80%, 90%) but not all of the possible methylase recognition sites for each enzyme in the methylase cocktail. A DNA sequence is partially methylated by treating DNA with an active methylase for a shorter period of time than is necessary to achieve complete methylation, and then terminating the reaction, or under other altered reaction conditions that allow for the desired amount of partial methylation.

The methylation densities of each sample in the series are measured by sequencing a statistically significant sample of clones from a bisulfite-treated portion of each series member in the set, by identifying the converted cytosines within each clone, and by calculating the average methylation density for each reaction within the methylation sample set. In order to achieve a partial methylation density on a given fragment, the methylase acts in a stochastic manner, and not a processive manner. For M.SssI, this is achieved by conducting the reaction in the presence of magnesium, since M.SssI methylates DNA in a processive way in the absence of magnesium, while in the presence of magnesium, the enzyme methylates CpGs in a non processive, stochastic manner.

Example 2

Quantitatively Determining the Relative Methylation of a Locus of Interest Between One Tissue and Another Tissue with Quantitative Amplification DNA is collected from two sources: a test population (diseased) and a control population (normal).

Each population of DNA fragments is similarly submitted to various partial or complete digestions with the enzyme McrBC. McrBC recognizes two $R^{M}C$ sites, each a half site, that are within 40 to 3,000 bases and with an optimal separation of the half sites of 50-103 bp and then cuts the DNA fragment sometimes 3' of both half sites, sometimes 3' of the 5' most half site and 5' of the 3' most half sites, and sometimes 5' of both half sites.

Next, the digested DNA in each population is amplified and the amount of the amplified locus is measured as a function of cycle number. The greater the number of methylated half sites in the locus of interest on a given DNA fragment within the population studied, the greater the probability that McrBC will cut between the PCR primers, and, therefore, a greater number of amplification cycles will be required to achieve the identical concentration of amplified PCR locus.

To determine whether the locus of interest within the test population is more or less methylated than the locus of interest within the control population, a concentration curve of amplified DNA of the test population is compared to the concentration curve of amplified DNA from the control population. Concentration curves reflect the amount of intact DNA as a function of the amount of digestion in a series of different partial digestions.

Example 3

Measuring the Methylation Density at a Locus of Interest within a Tissue with Quantitative Amplification DNA is obtained from a single source, and is divided into two populations. The first population of DNA is completely digested with the enzyme McrBC, while the remaining population is untreated. Alternatively, the first population is digested with a cocktail of one or more methylation sensitive restriction enzymes (e.g., HpaII, HhaI, or AciI, etc.), while the second population of DNA is untreated.

Next, the digested DNA in the first population is amplified and the amount of the amplified locus is measured as a function of cycle number. The greater the number of methylated half sites in the locus of interest on a given DNA fragment within the population studied, the greater the probability that McrBC will cut between the PCR primers, and, therefore, a greater number of amplification cycles will be required to achieve the identical concentration of amplified PCR locus. Alternatively, when a cocktail of methylation sensitive restriction enzymes is used, the greater the number of methylated restriction sites in the locus of interest on a given DNA fragment within the population studied, the lower the probability that the methylation sensitive cocktail of enzymes will cut between the PCR primers. Therefore, a lower number of amplification cycles will be required to achieve the identical concentration of amplified PCR locus.

To determine whether the locus of interest within the first population is methylated, a comparison is made between the kinetics of the amplification reaction profiles from the treated and untreated populations. Alternatively, to determine the density of methylation within the tissue at the locus of interest, the kinetics of the amplification reaction profiles are compared to those obtained from a known in vitro generated methylation sample set, i.e., a standard methylation curve.

Example 4

Measuring the Methylation Density at a Locus of Interest within a Tissue with Amplification End Point Analysis DNA is obtained from a single source, and is divided into a series of two or more portions.

This series is exposed to an increasing amount of partial digestion by a methylation dependent restriction enzyme, such as McrBC. The first portion of DNA fragments is untreated, the second portion is lightly digested with McrBC, and subsequent populations are more fully digested (but less than completely) with McrBC. The range of partial digestions is obtained through the manipulation of reaction conditions, such as the titration of enzyme amounts, digestion times, temperatures, reactants, buffers, or other required components.

Next, the DNA from the series of portions are amplified and the amount of amplified PCR loci is measured after a fixed number of cycles. The greater the number of methylated half sites in the locus of interest on a given DNA fragment within the first McrBC-treated portion, the greater the probability that McrBC will cut fragments of the first part between the PCR primers, and the greater number of amplification cycles will be required to detect a certain concentration of amplified PCR locus in the first portion.

To determine whether the locus of interest within the test population is more or less methylated, the results obtained from the series of portions and the parallel analysis of the standard sample set are compared (see Example 1).

Example 5

Quantifying Methylation Using Methylation-Sensing Isoschizomeric Partners and Quantitative PCR DNA is collected from two sources: a test population (diseased) and a control population (normal). Each population is divided into groups of two or more portions.

Each group is exposed to an increasing amount of partial digestion by a methylation sensitive restriction enzyme (e.g., HpaII, MboI (A)). The first portion of DNA fragments is untreated, the second portion is lightly digested with the methylation sensitive restriction enzyme, and subsequent populations are more fully digested (but less than to completion) with the enzyme. The range of partial digestions is obtained through the manipulation of reaction conditions, such as the titration of enzyme amounts, digestion times, temperatures, reactants, buffers, or other required components.

The second group of portions is similarly digested with an isoschizomeric partner of a different methylation-sensing class from the enzyme used to treat the first group of portions (e.g., MspI and Sau3AI (A), respectively). Alternatively, the second group of portions remains untreated.

Next, all of the portions in the groups are amplified and the kinetic reaction profile from each amplification is obtained. Alternatively, end point analysis after a fixed number of cycles is used.

To determine whether the locus of interest within the test population is more or less methylated, a comparison is made between the kinetic reaction profiles between the groups (group vs. group). Additionally, to determine whether the locus of interest between the two tissues is more or less methylated, a comparison is made between the kinetic reaction profiles between the populations (diseased groups vs. normal groups).

Example 6

Quantifying the Methylation Density of a Locus of Interest Using a Cocktail of Methylation Sensitive Enzymes DNA is obtained from a single source and is divided into groups of two or more portions. Alternatively, DNA is collected from two sources: a test population (diseased) and a control population (normal), and is divided into groups of two or more uniform portions.

The groups of uniform portions are treated with a fixed number of units of a cocktail of one of more methylation sensitive restriction enzymes (e.g., HpaII, HaeIII) for varied amounts of time.

Next, all of the portions in the groups are amplified and the kinetic reaction profile from each amplification is obtained. Alternatively, end point analysis after a fixed number of cycles is used.

To determine whether the locus of interest within the test population is more or less methylated, a comparison is made between the kinetic reaction profiles between the groups (group vs. group). Additionally, to determine whether the locus of interest between the two tissues is more or less methylated, a comparison is made between the kinetic reaction profiles between the populations (diseased groups vs. normal groups). Finally, the overall amount of methylation can be determined by comparing these results to those obtained from the standard sample set (see Example 1).

Example 7

Quantifying the Methylation Density of a Small Population of Methylated Alleles in the Presence of a Large Population of Unmethylated Alleles DNA is obtained from a single source and is divided into two portions. Alternatively, DNA is collected from two sources: a test population (diseased) and a control population (normal), and each population is divided into two portions.

To discriminate between methylated and unmethylated alleles, one portion from each population is treated with sodium bisulfite, which converts the unmethylated cytosine residues to uracil, leaving unconverted methylated cytosine residues. The bisulfite-treated portion is divided into two equal subportions. Alternatively, one portion from each population is digested with a cocktail of one or more methylation sensitive restriction enzymes (e.g., HpaII, HhaI, etc.), leaving the remaining portion untreated. The digested portion is similarly divided into two equal subportions.

One of the bisulfite-treated subportions is completely digested with the enzyme McrBC, while the remaining subportion is untreated. Alternatively, one of the methylation sensitive restriction enzyme-treated subportions is completely digested with the enzyme McrBC, while the remaining subportion is untreated.

One or both of the amplification primers are designed to resemble the bisulfite converted sequence overlapping at least one methylated cytosine residue. In this way, only those fragments that belong to the subset of fragments that were methylated at that primer in the test population have the potential of becoming amplified, while those fragments in the subset of fragments that remained unmethylated in the locus of interest will not be amplified. Alternatively, if methylation sensitive enzymes are used to discriminate between methylated and unmethylated alleles, then primers designed to the native sequence are used and only alleles that were methylated at the recognition sites remain intact and will be amplified.

Next, the DNA from both the McrBC-treated and McrBC-untreated portions, along with the relevant controls, are amplified and the amount of amplified PCR loci are measured as a function of cycle number.

To determine whether the locus of interest within the first population is methylated, a comparison is made between the kinetics of the amplification reaction profiles from the treated and untreated populations. To determine the density of methylation within the tissue at the locus of interest, the kinetics of the amplification reaction profiles are compared to those obtained from a known in vitro generated methylation sample set, i.e., a standard methylation curve.

Alternatively, this Example could also be performed by reversing the order of the sodium bisulfite conversion and the McrBC-digestion steps described above (i.e., McrBC digestion takes place prior to sodium bisulfite conversion).

In another alternative, partial digestion using McrBC is used in either a subportion or a series of subportions, instead of complete digestion.

Example 8

Demonstrating the Sensitivity of Detection

Human male placental DNA was obtained and was methylated in vitro using M.SssI, which methylates cytosines (5 mC) when the cytosines are followed by guanosine (i.e., GC motifs). The resulting in vitro methylated DNA was then mixed into unmethylated male placental DNA at known ratios, thereby producing a set of mixes, each comprising a different percentage of total copies that are methylated.

The various mixtures were then divided into three portions: an uncut portion; a portion digested with HhaI, a methylation-sensitive restriction enzyme that is sensitive to 5 mC and having the recognition sequence GCGC, where underlined nucleotides are unmethylated; and a portion digested with both HhaI and McrBC. McrBC is a methylation-dependent restriction enzyme that cleaves in the proximity of its methylated recognition sequence. The digested sequences were subsequently amplified using primers specific for a region upstream of the CDKN2A (p16) gene in the human genome [Ensembl gene ID# ENSG00000147889]. This region was determined to be unmethylated in human male placental DNA that has not been methylated in vitro. The primer sequences were:

```
Forward primer
                                          (SEQ ID NO: 2)
5'-CGGGGACGCGAGCAGCACCAGAAT-3', Reverse primer
                                          (SEQ ID NO: 3)
5'CGCCCCCACCCCCACCACCAT-3'
``` and standard PCR conditions were used:
 1 cycle [at 95° C. for 3 minutes]
 followed by 49 cycles at [95° C. for 30 sec, 65° C. for 15 seconds, and 68° C. for 15 seconds, a plate read (68° C.) and then another plate read at 83° C.].

The second plate reading at 83° C. was conducted to eliminate the fluorescence contribution of primer dimers to the reaction profile. A melt-curve, which measures fluorescence as a function of temperature, was performed between 80° C. and 95° C. at the end of the cycles and product specificity was determined. The locus of interest is 181 bp in length and has a melting temperature of approximately 89° C. Amplification product accumulation was determined using the intercalating dye, SYBR Green™ Dynamo Kit from MJ Research, which fluoresces when it binds to double stranded nucleic acids, and reactions were cycled and fluorescent intensity was monitored using the MJ Opticon II Real-time PCR machine.

A threshold at which the signal from the amplification products could be detected above background was determined empirically from a parallel analysis of a template dilution standard curve. The threshold was adjusted to maximize the fit of the regression curve (Ct vs. log [DNA]), according to standard threshold determination protocols familiar to those skilled in the art, such as those described in e.g., Fortin et al., *Anal. Biochem.* 289: 281-288 (2001). Once set, the threshold was fixed and the cycle thresholds (Ct) for each reaction were calculated by the software (MJ Research Opticon II Monitor V2.02). As expected, the derived cycle thresholds increased at higher dilutions of methylated to unmethylated DNA (FIG. 1). Also shown in FIG. 1, the change (or "shift") in cycle threshold (ΔCt) between uncut DNA and the HhaI treated DNA corresponded with that expected (E) for the dilutions, demonstrating that cycle threshold shift can be used to accurately predict the relative proportion of copies that are methylated in the sample out of the total number of copies in the sample.

FIG. 1 also illustrates that the addition of HhaI (a methylation sensitive restriction enzyme) and McrBC (a methylation-dependent restriction enzyme) further alters the Ct compared to the samples treated with HhaI alone. The degradation in the number of intact copies, and the resultant Ct shift to a higher Ct value after treatment with the methylation dependent restriction enzyme and the methylation sensitive enzyme further confirms the assessment that the intact copies present after treatment with the methylation-sensitive restriction enzyme alone are in fact methylated. In other words, this double digest provides a control against the possibility that HhaI was not added, was inactive, was partially active, or otherwise did not result in a complete digest. The addition of the methylation-dependent restriction enzyme and its ability to destroy methylated templates confirms the results observed after treatment with just the methylation-sensitive restriction enzyme and provides an internal control to assess the completeness of the methylation-sensitive restriction enzyme reaction.

Figure 2:
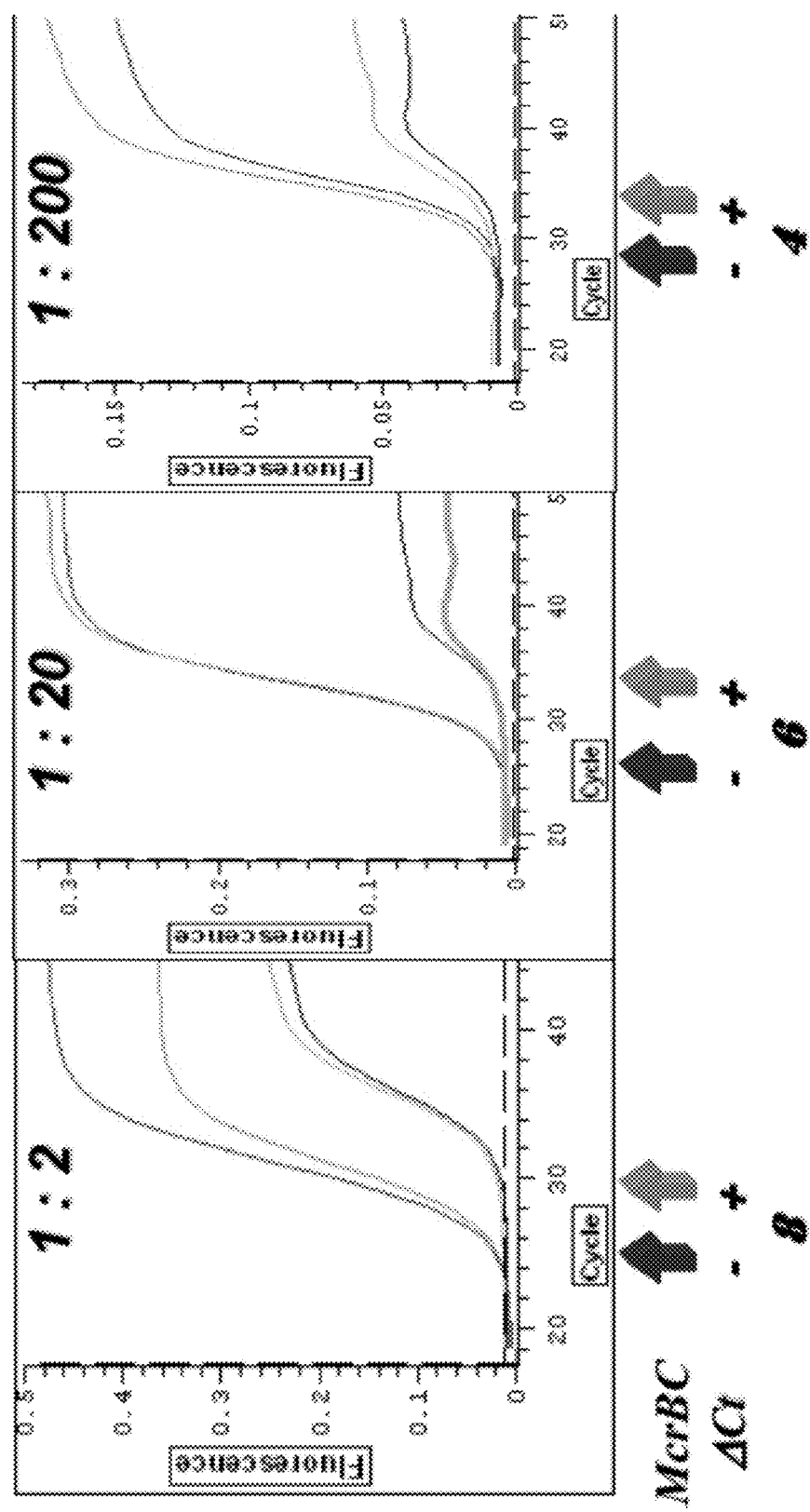
FIG. 2 illustrates the ability of McrBC to distinguish between DNA at different methylated:unmethylated dilutions. The arrows at the bottom of the figure indicate the approximate ΔCt between HhaI-cut and HhaI/McrBC double cut samples.

FIG. 2 depicts the kinetic profile of four portions at three dilutions of methylated DNA to unmethylated DNA. In each of the three dilutions, all four portions were digested first with the methylation sensitive restriction enzyme HhaI. The first two portions in each dilution were digested with McrBC, and the second two portions in each dilution were untreated with regard to McrBC. All portions were then amplified under identical conditions and the fluorescence intensities were measured. Three observations can be made. First, the duplicate reactions have nearly identical Ct values, demonstrating that the assays are highly reproducible. Second, decreasing change in Ct between treated and untreated portions as a function of increasing dilution of the methylated copies shows that as the methylated gene copies get more rare, there is less difference between the Ct values observed between the McrBC treated and untreated portions. This suggests that the HhaI and HhaI+McrBC reactions will converge and that at some point we will not be able to monitor methylation density or be able to identify the presence or absence of methylated copies. A theoretical extinction of detection will occur at a ΔCt of zero. Using a regression analysis, we solved for the extinction function in our system and found that the dilution where delta Ct=0 is 1:20,000, methylated copies to unmethylated copies respectively. This regression analysis is detailed in FIG. 4.

Figure 3:
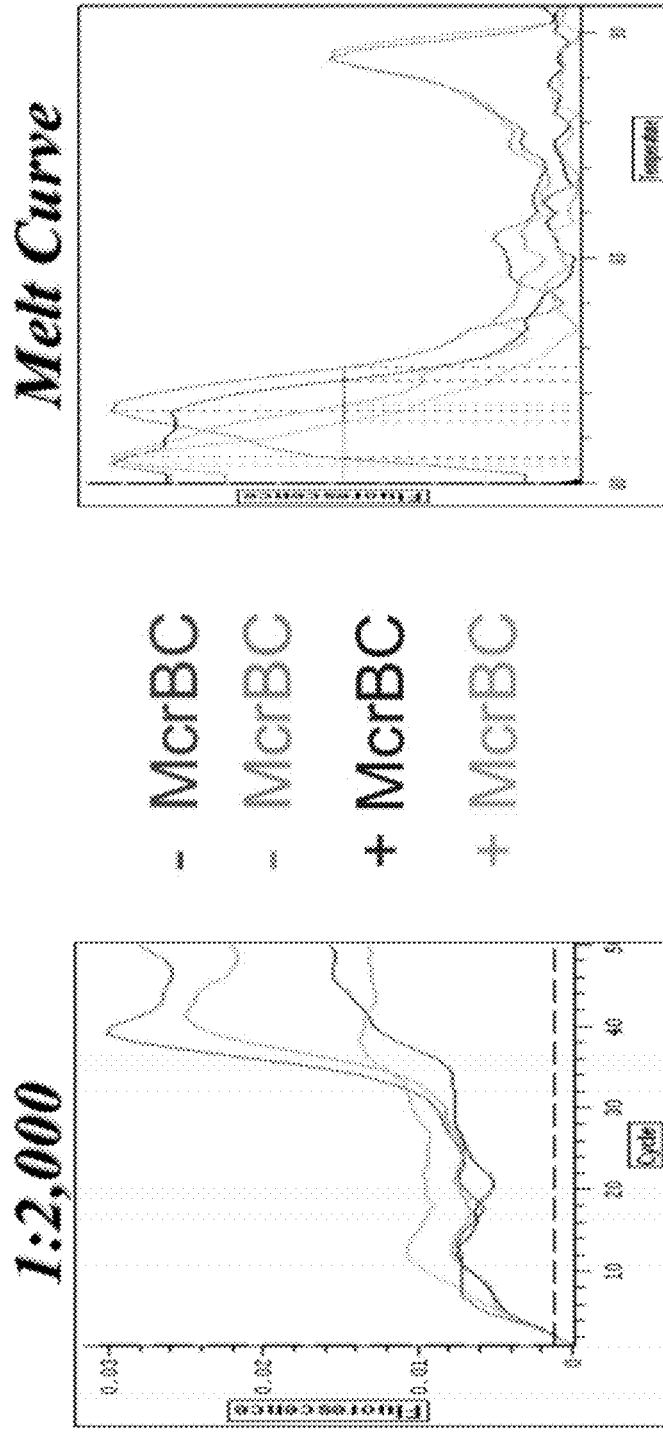
FIG. 3 illustrates analysis of DNA at a 1:2000 methylated:unmethylated dilution.

FIG. 2 shows the fluorescent kinetic profile of a series of portions all diluted to 1:2,000 methylated copies to unmethylated copies respectively. While the overall fluorescence obtained from the 1:2,000 reactions is not ideal, one can see a difference between the HhaI and the HhaI/McrBC reactions. Notice that the McrBC digestion destroys the accumulation of the fluorescence, and the melting point curve in FIG. 3 shows a specific peak at 89° C., which is the predicted melting temperature for the 181 bp specific amplicon. Here we are clearly detecting merely 1.4 cellular equivalents of methylated DNA diluted into a total of 2,762 cellular equivalents of DNA.

Figure 4:
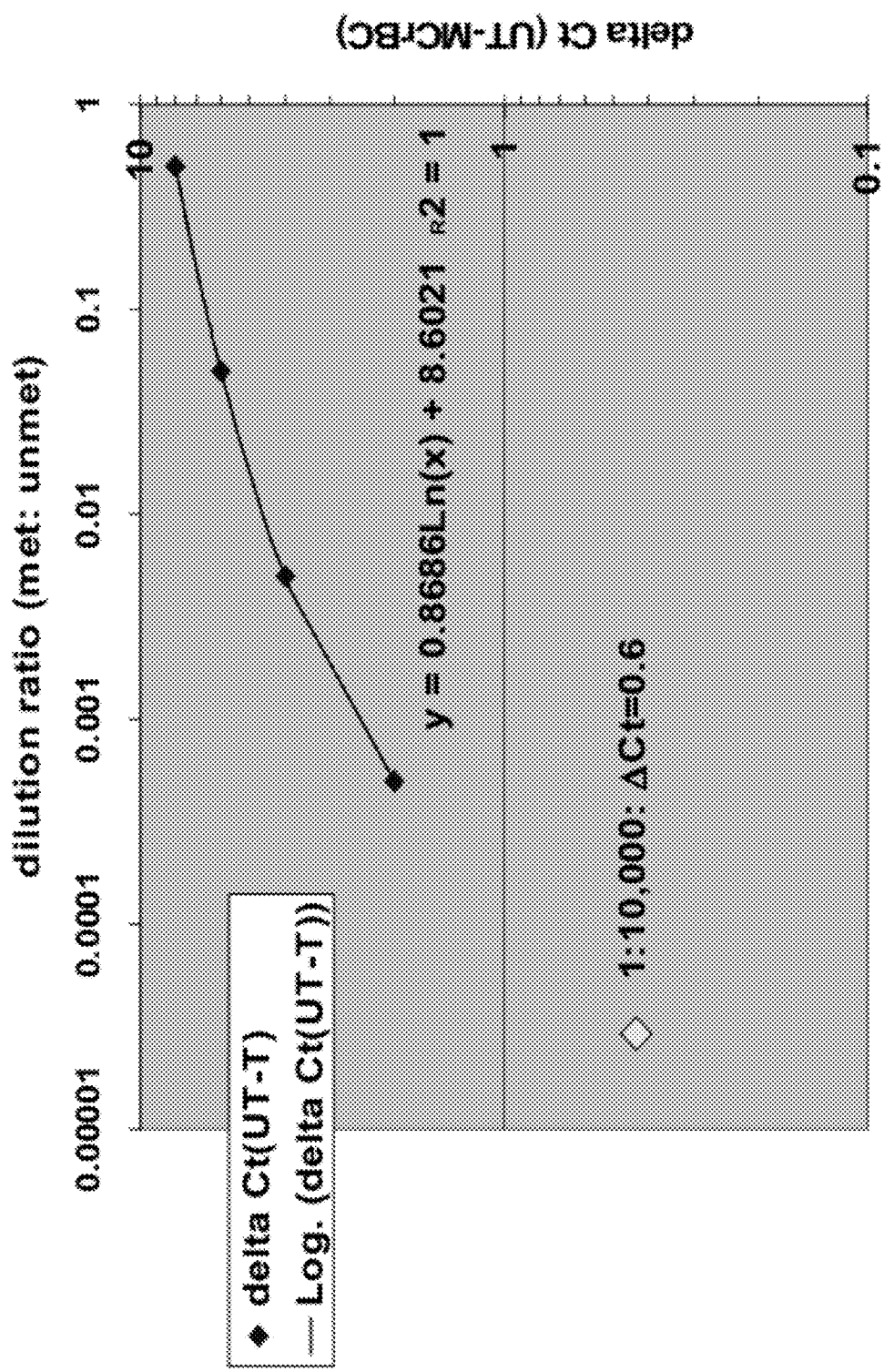
FIG. 4 illustrates a plot of change in cycle threshold as a function of dilution of methylated/unmethylated DNA.

As shown in FIG. 4, 1.4 cellular equivalents (CE) were detected out of a total of 2,764 CE in the tube having a total of 20 ng of genomic DNA. Each cellular equivalent has approximately 7.9 pg of genomics DNA per cell. Thus, if 50 ng of genomic DNA is used, one methylated copy in the presence of 10,000 unmethylated copies should be detectable. This principle is illustrated in FIG. 4. FIG. 5 provides a breakdown of this analysis. Note that this detection limit can be further lowered by (i) using an optimized FRET-based probe, rather than an intercalating dye, to detect amplified products, (ii) by further optimizing PCR primer design, or (iii) by further optimizing PCR reaction conditions.

Example 9

Detecting Methylation Density

Figure 6:
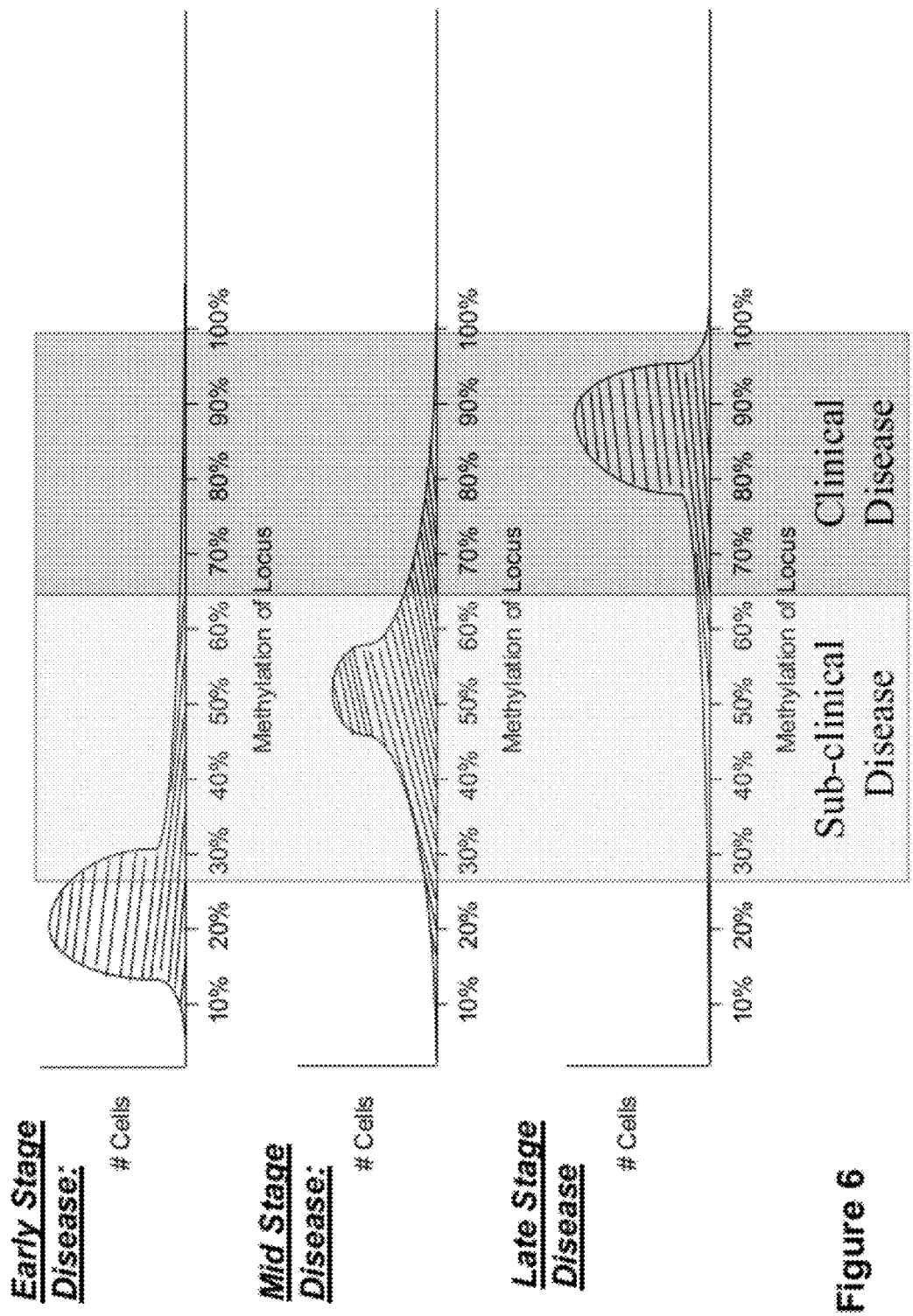
FIG. 6 illustrates a hypothetical methylation density progression in the development of disease.

This example demonstrates determining the average density of methylation (i.e., the average number of methylated nucleotides) within a locus. As provided in FIG. 6, it is likely that in many diseases, methylation of one or more loci goes through a progression of increased methylation density corresponding to disease progression. Previously-described methylation detection techniques involve detecting the presence or absence of methylation at one or more particular nucleotides but do not provide analysis of density across a locus. In contrast, the present invention provides methods for detecting the average number of methylation events within a locus.

Figure 11:
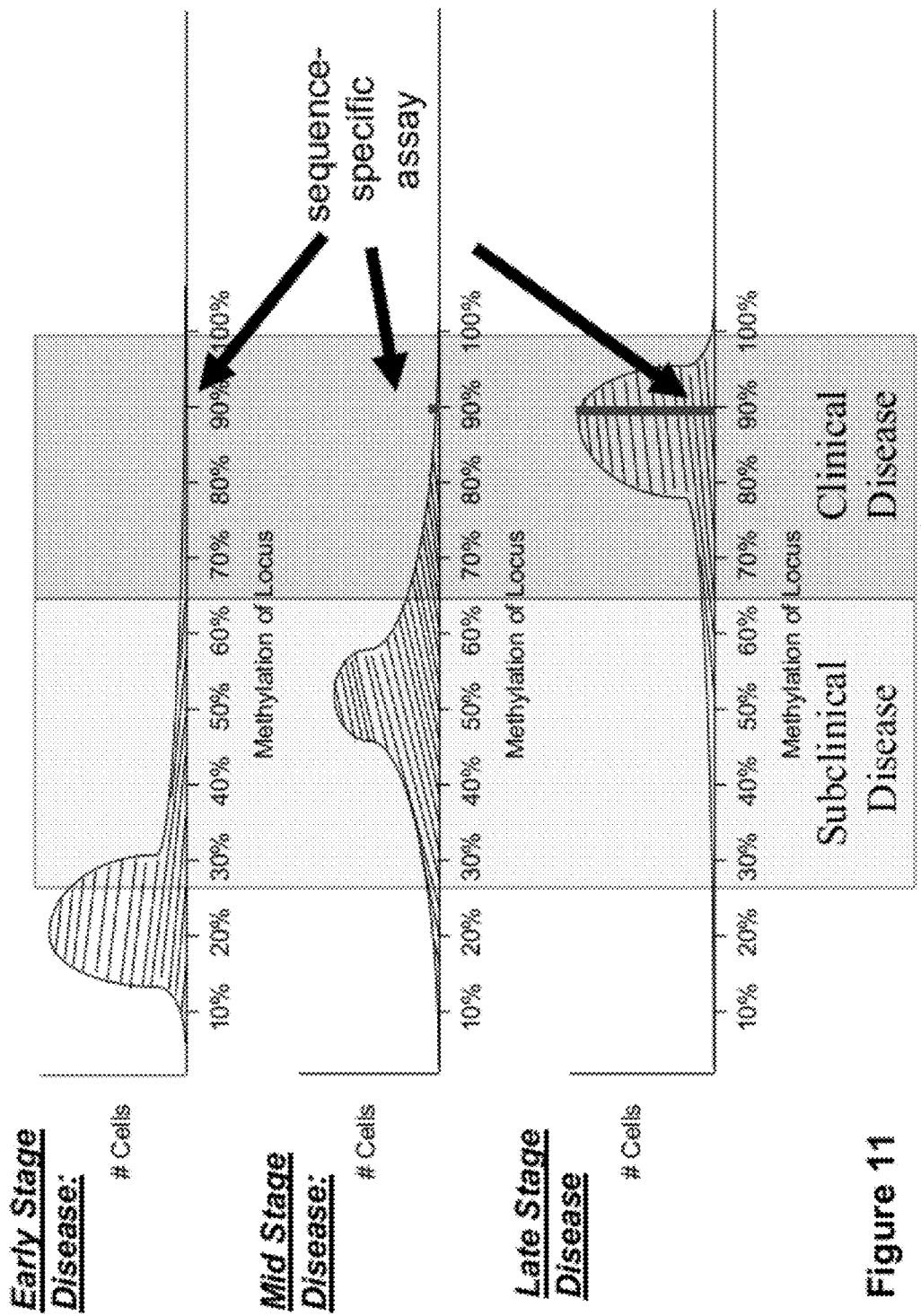
FIG. 11 illustrates what data is obtained when the methylation state of only particular nucleotides is detected in a hypothetical disease progression.
Figure 12:
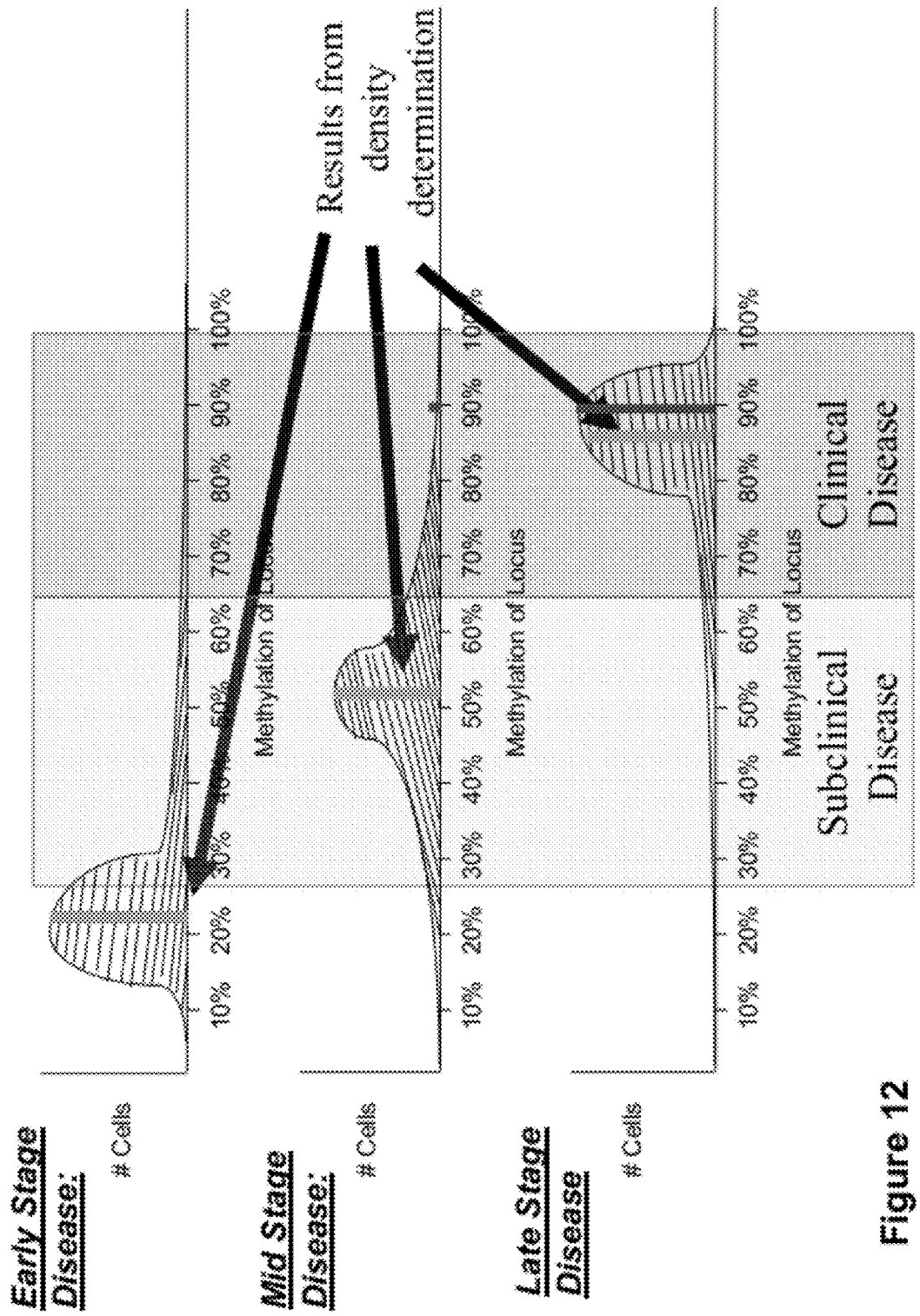
FIG. 12 illustrates what data is obtained when the average methylation density of a locus is detected in a hypothetical disease progression.

As illustrated in FIGS. 11-12, methods that detect methylation at only specific short sequences (typically relying on primer or probe hybridization) may miss changes in methylation (see FIG. 11) that the present methylation density detection methods (which examine relative methylation across an entire locus) are able to detect (see FIG. 12).

This discovery works by treating a locus with a methylation-dependent or methylation-sensitive restriction enzyme under conditions such that at least some copies of potential restriction enzyme cleavage sites in the locus to remain uncleaved. While these conditions can be achieved by allowing for partial digestion of a sample, the particular recognition and cutting activity of McrBC allows for additional options.

As discussed above, when two McrBC complexes meet, restriction occurs, typically within ~32 bp of either half site (i.e., in one of four regions). See FIG. 7. Restriction does not occur if half sites are closer than 20 bp.

Since McrBC randomly cuts 5' or 3' of the recognized pair of half sites, the probability of cutting at a locus (spanned by primers in the case PCR) is function of the number of methylated half-sites present at or near the locus. For a set concentration of enzyme and time of incubation, the more methylation sites within a locus, the greater the probability McrBC will cut at the locus (or between the primers in the case of PCR). However, under ideal circumstances and sufficient number of DNA copies, the probability that McrBC will cut every copy of a locus is low because it will sometimes cut at a distance outside of the locus, thereby leaving the locus intact. Thus, the number of intact loci is inversely proportional to the average number of methylated nucleotides within the locus. The number of intact loci is inversely proportional to the Ct value for a given sample. Thus, the Ct value is proportional to the average number of methylated nucleotides within a locus. Thus, comparison of the Ct value of amplified McrBC-treated DNA compared to the Ct value from amplified untreated DNA allows for the determination of methylation density of the locus.

Figure 8:
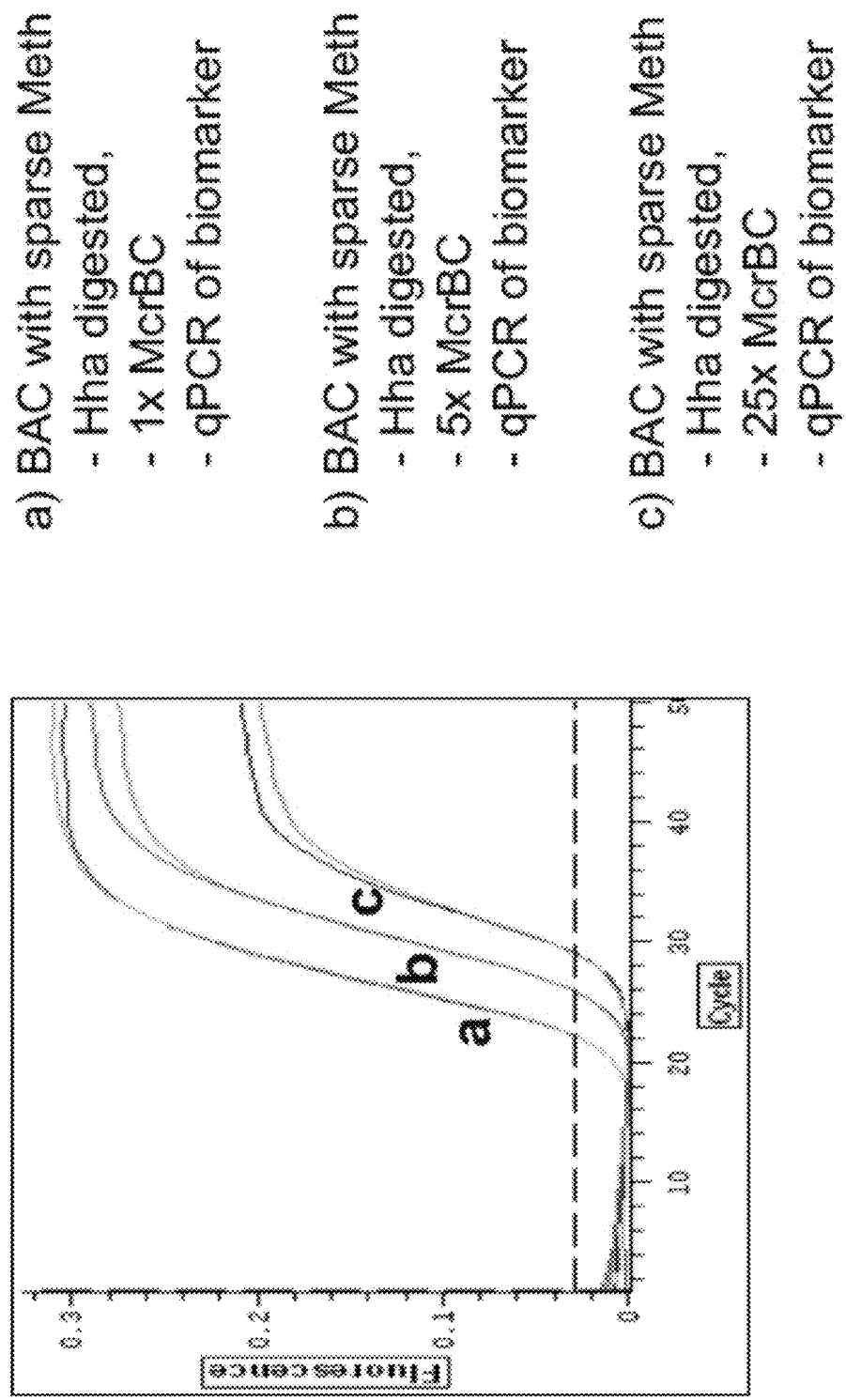
FIG. 8 illustrates amplification results from different McrBC dilutions restricting sparsely-methylated DNA.
Figure 9:
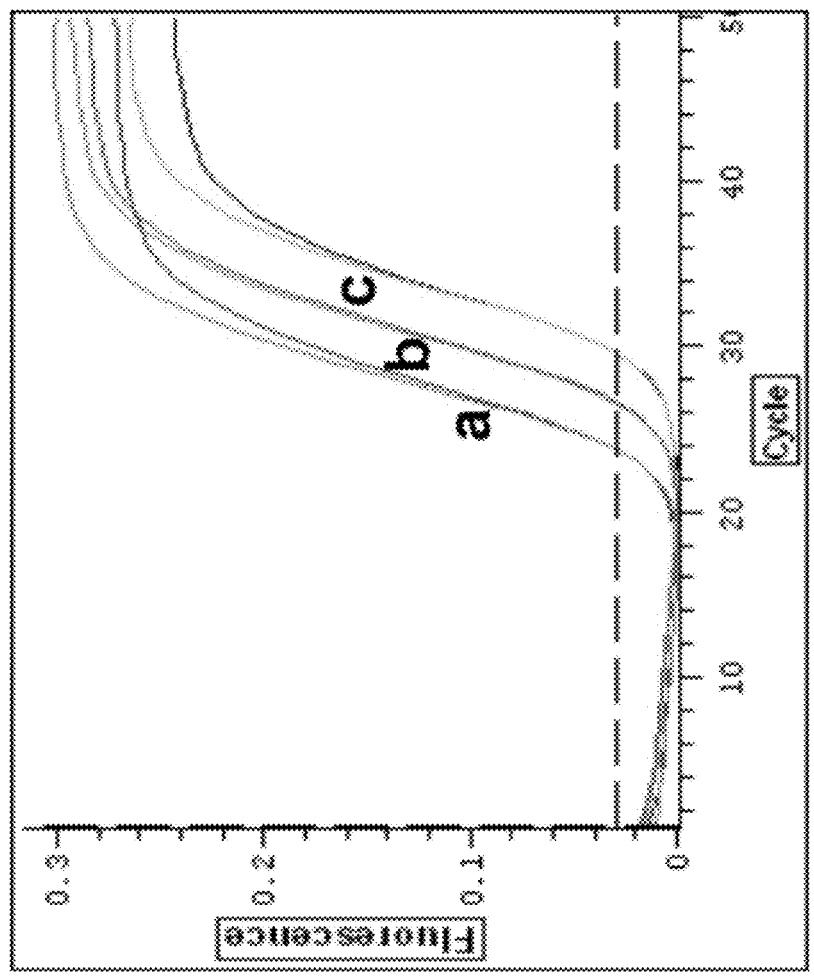
FIG. 9 illustrates amplification results from different McrBC dilutions restricting densely-methylated DNA.
Figure 10:
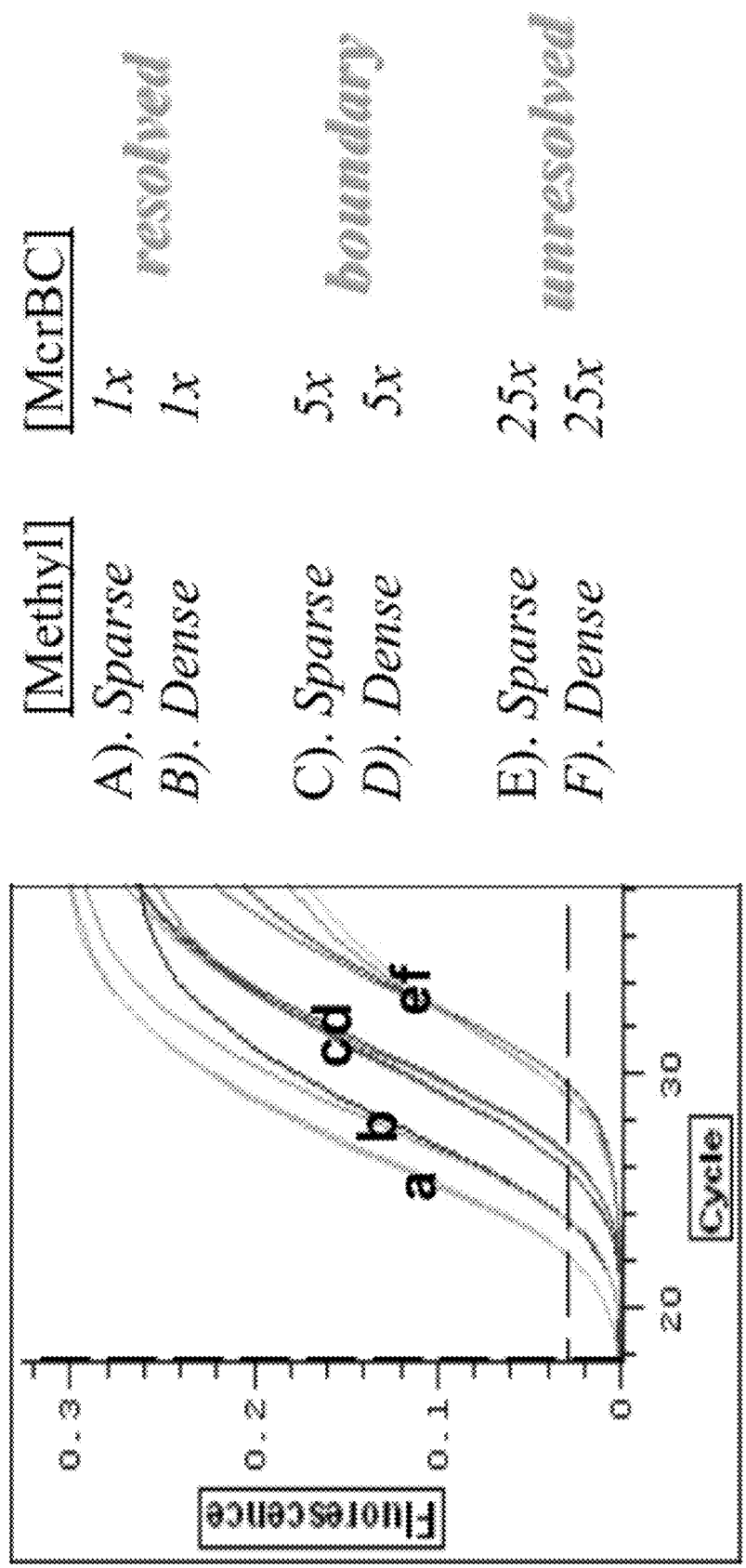
FIG. 10 illustrates using different restriction enzyme dilutions to determine optimum resolution between DNA with different methylation densities.

Two aliquots of BAC DNA containing the p16 locus was in vitro methylated at different densities. The first aliquot was densely methylated with M.sssI. There are 20 M.sssI methylase sites within the PCR amplicon, 11 of which are also McrBC half-sites. The second aliquot was sparsely methylated with M.HhaI. There are four M.HhaI methylase sites within the PCR amplicon, all four of which are also McrBC half-sites. Within the PCR amplicon there are also 4 restriction sites for HhaI. All four of these HhaI restriction sites are methylase sites for both M.sssI and M.HhaI, such that complete treatment with either methylase will protect all four HhaI sites from restriction. A different number of units of McrBC was used for a set period of time (four hours) to generate a series of progressively more partial digestions to identify an amount of enzyme to best allow for distinguishing results from the sparsely and densely-methylated DNA. As displayed in FIGS. 8 and 9, the Ct values were proportional to the concentration of McrBC used in both sparsely and densely-methylated sequences. FIG. 10 demonstrates results from titrating different amounts of McrBC to enhance resolution between sparsely and densely methylated sequences to distinguish between the two. In FIG. 10, "1×" equals 0.8 units of McrBC as defined by New England Biolabs.

The densely methylated target has 2.75-fold more methylated McrBC half sites than the sparsely methylated target (11/4=2.75). Therefore, upon treatment with McrBC and subsequent amplification, we expect to see a difference between the Ct of the reactions of about 1.46, as $2^{\Delta Ct}=2.75$. Solving for $\Delta Ct$, $\Delta Ct=\log(2.75)/\log(2)=1.46$. We observed $\Delta Ct$ (sparse–dense @ 1× McrBC) was 1.51±0.05. Thus, the methylation density of a locus was determined using this method.

Example 10

Bisulfite-Coupled Methylation Density Determination

This example demonstrates the ability to determine the methylation density of a locus by treatment with both bisulfite and a methylation dependent restriction enzyme followed by PCR amplification and quantitation of the amplified products.

Two samples of DNA, one purified from human blood cells and the other purified from a glioma cell line, were treated with bisulfite. The samples were then each split into two portions, one portion from each was digested with McrBC, while the other portion was mock-digested (i.e. was not digested with McrBC). Since methylation (5 mC) is protected from bisulfite conversion, all McrBC sites remain intact in the converted DNA.

From each of the four portions, 1 μL, 2.5 μL and 5 μL, respectively, was utilized as template for PCR amplification, resulting in 12 PCR reactions. A no template negative control and a bisulfite treated positive control were also analyzed. PCR primers, which were designed to anneal to the bisulfite converted sequence of a locus of interest, and PCR reagents were used in the 12 PCR reactions and in the positive and negative control reactions. PCR amplification of the locus was conducted for a number of cycles determined to be limiting and equal volume aliquots of the amplifications were evaluated with agarose gel electrophoresis.

Figure 14:
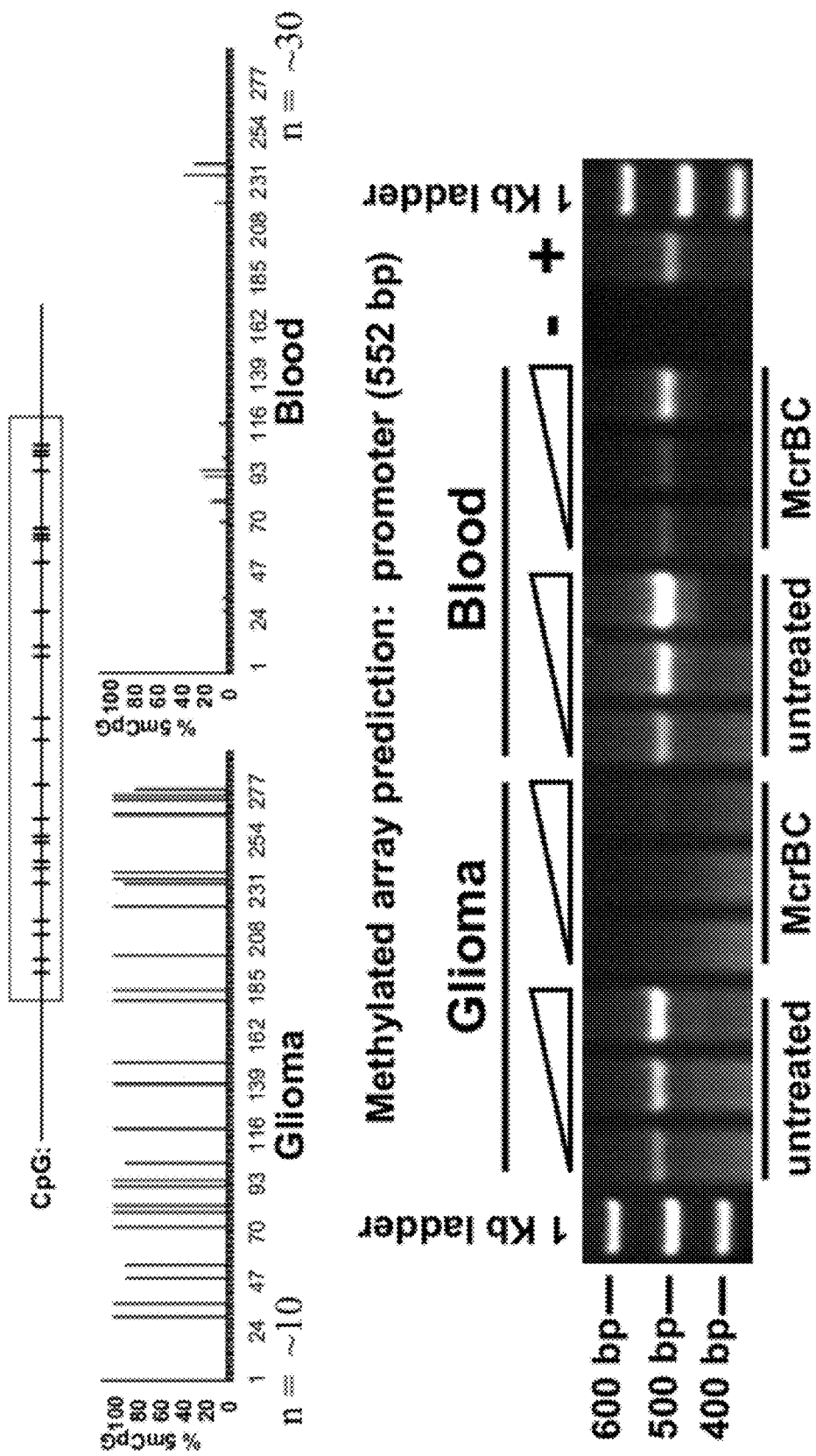
FIG. 14 illustrates analysis of McrBC/amplification-based methylation detection and comparison to bisulfite sequencing. The data was generated using bisulfite treatment, McrBC digestion, and then amplification.

The lanes labeled "untreated" in the agarose gel image in FIG. 14 represent bisulfite converted DNA from glioma (left) and blood (right) that were not digested with McrBC. The lanes labeled "McrBC" in the agarose gel image in FIG. 14 represent bisulfite converted DNA from glioma (left) and blood (right) that were digested with McrBC. McrBC treatment resulted in a decrease in PCR amplicon signal from both samples, suggesting that both samples contain at least some 5 mC. Additionally, PCR amplicon signal of the McrBC treated blood aliquots was greater than the PCR amplicon signal of the McrBC treated glioma aliquots, suggesting that the density of McrBC in the glioma sample was greater than the density of McrBC in the blood sample.

To independently determine the density of methylation in the samples, bisulfite sequencing was performed on approximately ten and thirty cloned PCR amplicons from the bisulfite treated glioma and blood samples, respectively. Sequence analysis was conducted to tabulate the percentage of methylation at each CpG in the locus of interest for each of the samples. CpG positions in the locus are indicated as tick in the top line in FIG. 14, and the second row of graphs in FIG. 14 depicts methylation density of each CpG in each sample. The bars (red in the glioma graph and green in the blood graph) illustrate the percentage of times that each CpG was sequenced as methylated (i.e., it was sequenced as "C" rather than "T" following bisulfite treatment, amplification and cloning and sequencing). The absolute methylation density determined by bisulfite sequencing was 92% in Glioma cells and 7% in normal blood cells. The independent confirmation and the McrBC-coupled bisulfite PCR results above agreed.

Example 11

Methylation Density Determination

This example demonstrates the ability of methylation-dependent and methylation-sensitive restriction enzymes to distinguish different methylation densities at a locus.

Figure 15:
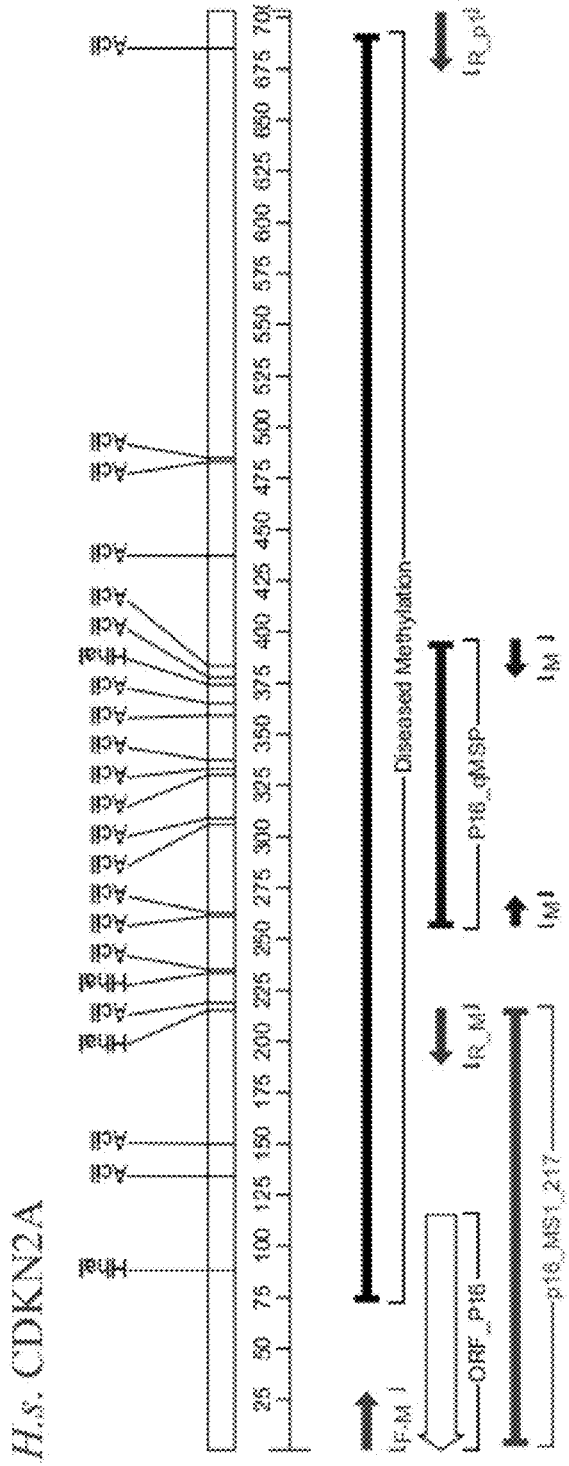
FIG. 15 depicts a portion of the p16 promoter (SEQ ID NO:1) methylated in vitro with M.Sss I.

A 703 bp portion of the promoter of p16 was amplified. The portion was methylated in vitro in a time course with M.SssI under conditions that promote stochastic methylation. The portion is illustrated in FIG. 15. From the large methylation reaction at different time points, fixed volumes (20 μl) were removed and the methylation reactions were stopped with heat (65° C.). We stopped one reaction before it began (T=1 is 0 minutes methylation, i.e., the unmethylated control; T=2 was stopped at 2 minutes; T=3 was stopped at 5 minutes; and T=4 was stopped at 60 minutes, a time at which the PCR product in the reaction should have been fully methylated.

The reactions were purified and each amplicon then was diluted more than 1 million fold in TE buffer, and was added back to the human genome at a ratio that should approximate a normal copy balance (i.e., two copies per 7.9 picograms). The human genome used was homozygous for a deletion of the p16 gene. The deletion cell line is CRL-2610. This allowed us to add a fixed amount of the human genome (i.e., control for the complexity of the genome in our reaction).

DNA samples were cleaved with Aci I (a methylation-sensitive restriction enzyme), McrBC (a methylation-dependent restriction enzyme), or both as double digest, and the portion was amplified. Amplicons were detected with the MS_p16(207) SYBR green real-time PCR system. Twenty nanograms of input DNA (genome+amplicon) equal ~2764 cellular equivalents/per PCR reaction. Each set of four digests was brought up to volume in restriction salts with BSA and GTP such that it could be split into four tubes (~4 μg). Each of the four digest tubes (~1 μg) had 100 μl total volume such that 2 μl could be added to PCR reactions, thereby adding 20 ng of DNA. Digests were allowed to proceed for four hours and were heat killed for 20 minutes. PCR conditions:

```
                                         (SEQ ID NO: 4)
       CAGGGCGTCGCCAGGAGGAGGTCTGTGATT = F primer (SEQ ID NO: 5)
       GGCGCTGCCCAACGCACCGAATAGTTACGG = R primer
```

Dynamo MJ qPCR buffer, 65° C. anneal, two cycle PCR (95° C. 30 sec, 65° C. 20 sec) cycled 49 times and monitored with an MJ opticon II quantitative PCR system.

We hypothesized that if the technology is monitoring density:

a) The McrBC cleavage should demonstrate a larger ΔCT for each sample in a progression from 0 ΔCt for T=1, up to a maximal ΔCt at T=4 (60 minutes)

b) The Aci I reactions should demonstrate the inverse relationship.

c) The mock treated and double digests should be fixed reference points

As illustrated in FIG. 16, we observed the trends outlined above. The McrBC curve moves oppositely from the Aci I curve, and the movement is in proportion with the increasing methylation content in the locus. The untreated and double digests indicate the boundaries of the assay field. The system resolves the difference between each of the reactions along the time course, such that each graphical depiction showing the various timed reactions is different. The point where the profile intersects the dashed threshold line indicates the point where information is compared.

Figure 17:
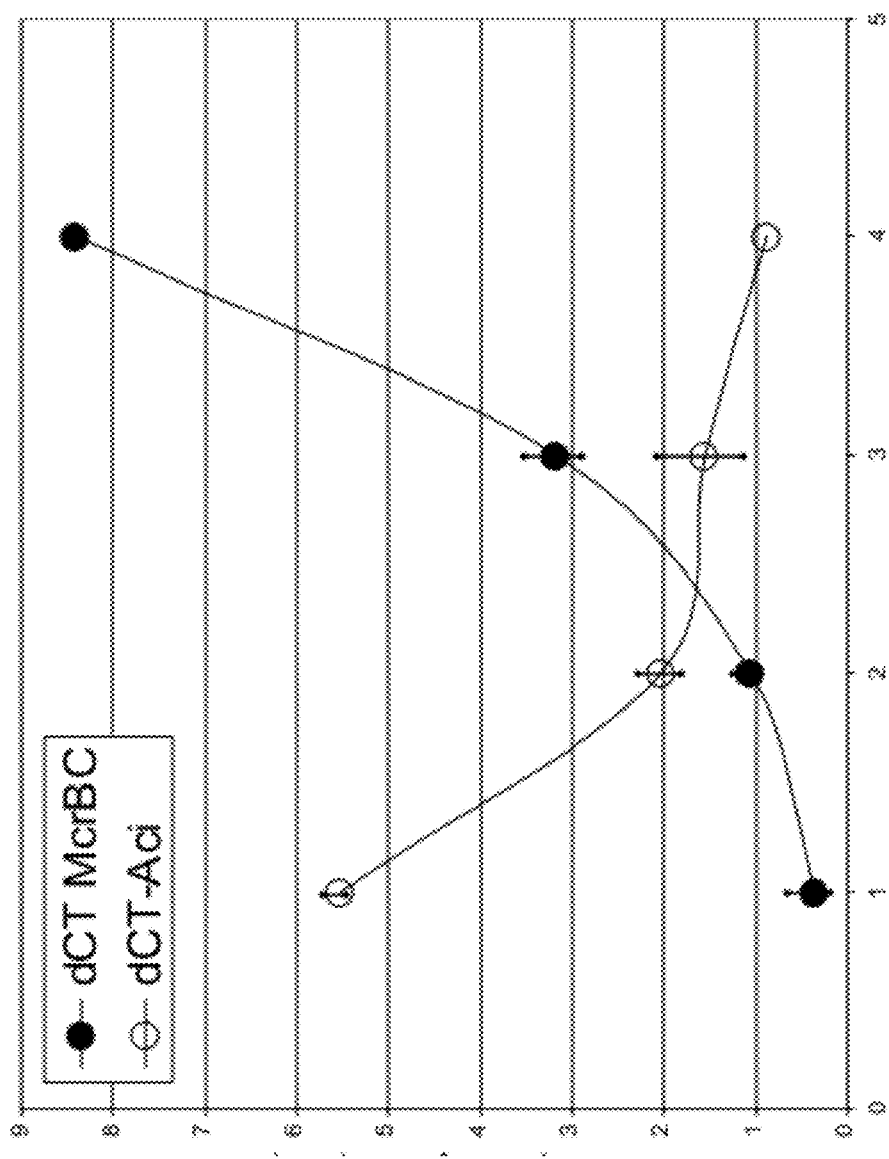
FIG. 17 illustrates cycle threshold data demonstrating that methylation-dependent (i.e., McrBC) and methylation-sensitive (i.e., Aci I) restriction enzymes distinguish different methylation densities at a DNA locus.

Another way to visualize the data is by plotting the change in cycle threshold values (ΔCt). See FIG. 17. FIG. 17 displays the ΔCt for McrBC-treated compared to untreated at each time point in the partial methylation reaction, and the corresponding ΔCt for the Aci I digests (Aci I compared to untreated). As expected, the McrBC and Aci I ΔCt lines provide an intersecting inverse pattern. The Aci I graph displays a chunky shape because its cut sites are fixed, while McrBC displays a smooth continuous distribution, reflecting its ability to cut more or less randomly following site recognition. Frequency of cutting is proportional to the expected change in methylation occupancy based upon the time course. The error bars associated with the real-time measurements are indicated. If they are not visualized, they are within the data point.

Example 12

Monitoring DNA Methylation of a Target Sequence Present at Multiple Locations in the Genome This example demonstrates the ability of the present technology to determine the methylation of a target sequence that is present in a genome more than one time (i.e., more than one copy) using an assay that monitors a sequence repeated in the kafirin gene cluster in *Sorgum bicolor*.

Eleven kafirin genes were annotated from the publicly available sequence of a BAC clone AF527808 from *Sorghum bicolor*. PCR primers were designed to amplify a 247 bp amplicon form all 11 kafirin genes (the primer sequences were conserved in all 11).

```
       The forward primer was
                                         (SEQ ID NO: 6)
       5' CTCCTTGCGCTCCTTGCTCTTTC 3'

The reverse primer was
                                         (SEQ ID NO: 7)
       5' GCTGCGCTGCGATGGTCTGT 3'
```

Sorghum genomic DNA isolated from seedling leaf was divided into 6 equal portions. The six portions were treated in the following manner: i) untreated (mock treated), ii) HhaI digested, iii) McrBC digested, iv) HhaI and McrBC digested, v) PstI digested and, vi) PstI and McrBC digested. Equal volume aliquots from the six portions were amplified using the above PCR primers in the following manner:

The SYBR green real-time PCR cycling parameters were 95° C. for 3 minutes, followed by 50 cycles of 2 step PCR 95° C. for 30 sec, 56° C. for 30 seconds with the Dynamo Kit from MJ Research (Boston, Mass.). We utilized both a low temperature (70° C.) and a high-temperature plate read (82° C.). The input of genomic DNA was 10 ng per PCR reaction. The threshold was set using a template dilution standard control.

Figure 19:
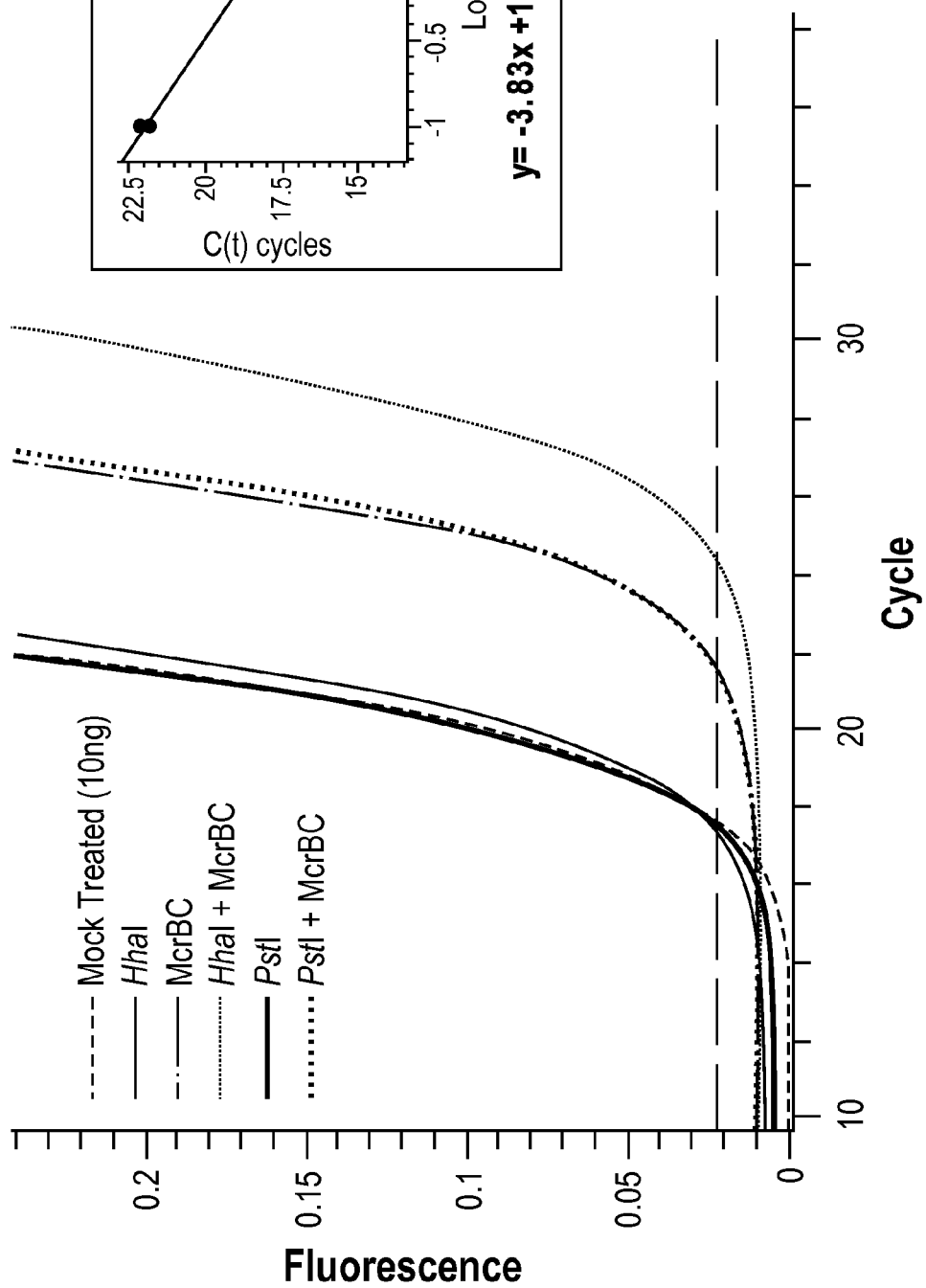
FIG. 19 illustrates the heterogenous CG methylation and homogenous CNG methylation of eleven kafirin genes.

The kinetic profiles for the 6 PCR reactions are depicted in FIG. 19. The inset in FIG. 19 depicts the template dilution standard curve used to set the cycle threshold for the experiment. Each set of 6 digests was performed three times, and each of the 18 digests had four PCR replicates. The PCR reactions were determined to be highly reproducible. In FIG. 19, PCR amplification reaction kinetics for each of the six digestions are depicted with different colors: Red=mock treated, Blue=McrBC digested, Orange=HhaI digested, and Green=HhaI+McrBC double digest, Pink=PstI, and Azure=PstI+McrBC double-digest. Comparisons between the cycle thresholds of the six amplified digestions were made and of the density of CNG and CG methylation in the repeated target sequence was determined.

In all 11 kafirin genes, all PstI sites in the repeated target sequence were methylated (at CNG) and PstI digestion was blocked since the PstI treated sample (pink) has the same cycle threshold (Ct) as the mock treated sample (red). This result is supported by the McrBC digested sample (blue), which has a significantly higher Ct than the mock-digested DNA control (red), further demonstrating that CNG methylation exists because McrBC was able to cut, thereby lowering the number of intact copies of the target sequence. All, or almost all, of the PstI sites are methylated because the double PstI+McrBC digest (light blue) has the same Ct as McrBC alone (blue). Note that the McrBC digestion with and without PstI yields the same Ct, while HhaI with McrBC (green) yields a higher Ct on average; suggesting that not all HhaI sites were methylated and that HhaI was able to reduce the number of intact copies of the target sequence. These results indicate that every target sequence has high CNG methylation covering all PstI sites, while some but not all HhaI sites are methylated, indicating partial CG methylation of HhaI sites in the target sequence. The specificity of each reaction was confirmed using melt-curve analysis.

Figure 18:
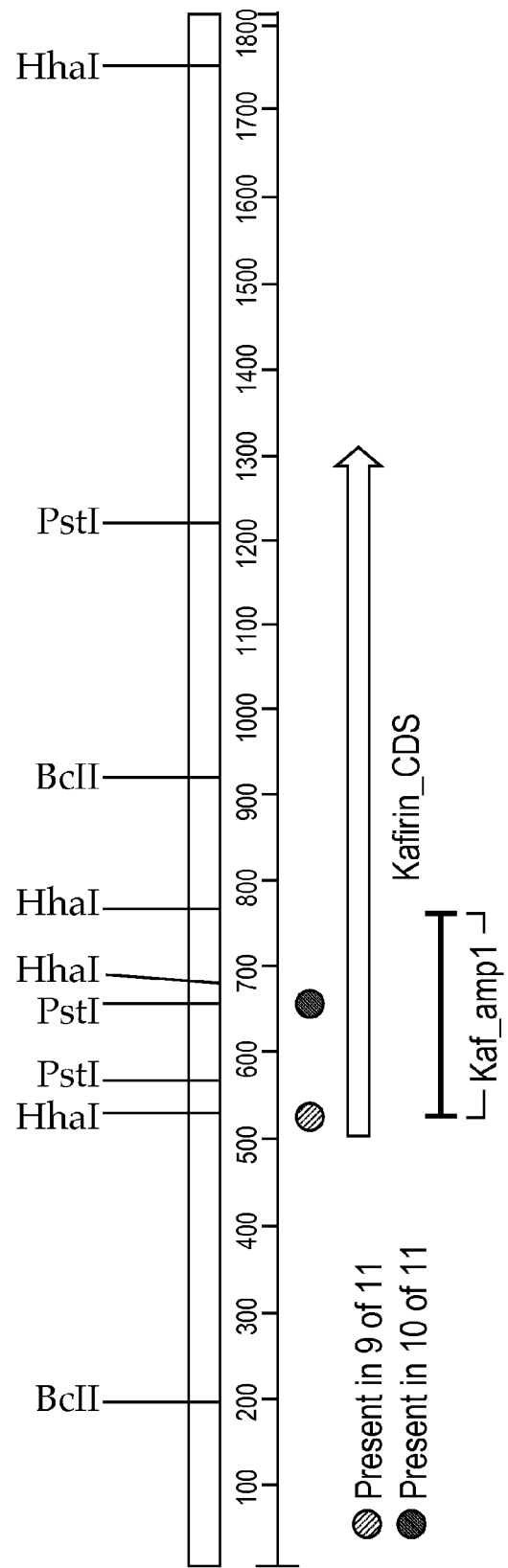
FIG. 18 illustrates a consensus restriction map of kafirin genes. The relevant restriction sites are indicated vertically and the numbers indicate the distances scale in base-pairs. Each coding sequence is depicted as the blue-shaded arrow, and the region assayed is indicated by the black bar. The circles depict sites that are not present in every kafirin gene, and the color represents the number of genes that do not share the site. The orange circle (5' most HhaI site) is conserved in 9 of 11 Kafirin genes, and the red circle (3' most PstI site) is present in 10 of the 11.

For the kafirin genes, the average difference in Ct between the McrBC single and HhaI+McrBC double digests is 2.46 cycles (22.08±0.34 HhaI+McrBC−19.62±0.19 McrBC). We compared the cycle-thresholds of genomic DNA that had been subjected to various treatments and inferred methylation occupancy through the changes in Ct mediated by the treatments. The Ct of any locus is a function of the number of copies present within the assay tube. Each of the eleven genes was broken into ~1.5 kb pieces which were aligned to create a consensus kafirin assembly (FIG. 18). The consensus kafirin sequence was examined and PCR primers amplifying a 247 bp amplicon were selected (see above).

As for CG methylation, the HhaI digested (orange) sample has the same Ct as the mock treated control (red); however, the HhaI+McrBC double digest (green) has a Ct that is 2.46 cycles greater than the McrBC alone (blue), indicating that some HhaI sites must not be modified. A cycle threshold difference of 2.46 indicates that there is $2^{2.46}$, or approximately 5.5-fold, less DNA in the HhaI+McrBC double digested sample. This suggests that 2 out of the 11 kafirin genes have some unmethylated HhaI sites.

To independently confirm the presence of methylation at the repeated target sequence, a 1× shotgun sequence was generated of the methyl filtered sorghum genome (See U.S. Patent Publication No. 20010046669, Bedell et al., PLOS in press). 95% of the genes in the sorghum genome were determined to be represented in the methyl filtered sequence set. In the kafirin gene cluster, however, only 2 of 11 genes from BAC clone AF527808 were represented in the methyl filtered sequence set, suggesting that most or all of them may be methylated, and therefore are underrepresented in the methyl filtered sequence. Ten of the genes are tandemly arrayed in a cluster and share an average of 99.1% sequence identity, while the eleventh gene is located 45 kb away and is more diverged (76.2% identity on average). A 247 bp region was selected for PCR close to the 5'end because of its near identity across all 11 genes and because of the high CG and CNG content (see FIG. 18). The independent confirmation of methylation at the target sequence agreed with the methylation determination made by analysis of the reaction kinetics of the amplified digested DNA.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference.

What is claimed is:

1. A method of calculating the relative methylation density for a target locus in a DNA sample, the method comprising,
   i. contacting a first portion of the DNA sample with a methylation-dependent restriction enzyme under partial digestion conditions where the resulting number of remaining intact copies of the locus is inversely proportional to the quantity of methylation at the locus;
   ii. quantitatively amplifying intact copies of the locus in the DNA sample after step i;
   iii. identifying a cycle-threshold (Ct) value from step ii;
   iv. quantitatively amplifying intact copies of the locus in a second portion of the genomic DNA that has not been cut by a restriction enzyme;
   v. identifying a cycle-threshold (Ct) value from step iv; and,
   vi. determining the relative methylation density for the target locus by calculating the difference ($\Delta$Ct) between the Ct from step iii and the Ct from step v, wherein $2^{|\Delta Ct|}$ is proportional to the relative methylation density.

2. A method for detecting methylation density in a locus of genomic DNA, the method comprising:
   a. contacting a first portion of the genomic DNA containing the locus with a methylation-dependent restriction enzyme under partial digestion conditions where the resulting number of remaining intact copies of the locus is inversely proportional to the quantity of methylation at the locus;
   b. quantifying the remaining intact copies of the locus in the first portion following step a;
   c. quantifying intact copies of the locus in a second portion of the genomic DNA that has not been cut by a restriction enzyme, wherein comparison of the quantity of intact copies of the locus in step b to the quantity of intact copies of the locus in step c allows for methylation density detection.

3. The method of claim 2, further comprising: contacting a third portion of the genomic DNA with a methylation-sensitive restriction enzyme and the methylation-dependent restriction enzyme to generate intact and cleaved copies of the locus; quantifying the intact copies of the locus in the third portion following methylation-sensitive restriction enzyme and methylation-dependent restriction enzyme digestion.

4. The method of claim 3, further comprising: contacting a fourth portion of the genomic DNA with a methylation-sensitive restriction enzyme to generate intact and cleaved copies of the locus; quantifying the intact copies of the locus in the fourth portion following methylation-sensitive restriction enzyme digestion.

5. The method of claim 2, further comprising: contacting a third portion of the genomic DNA with a methylation-sensitive restriction enzyme to generate intact and cleaved copies of the locus; quantifying the intact copies of the locus in the third portion following methylation-sensitive restriction enzyme digestion.

6. The method of claim 2, wherein the quantifying steps comprise hybridizing two oligonucleotide primers to genomic DNA flanking the locus to produce an amplification product corresponding to the intact copies of the locus of genomic DNA between the primers.

7. The method of claim 6, wherein the quantifying steps comprise quantitative amplification of the intact copies of the locus.

8. The method of claim 3, wherein the quantifying steps comprise quantitative amplification of the intact copies of the locus.

9. The method of claim 4, wherein the quantifying steps comprise quantitative amplification of the intact copies of the locus.

10. The method of claim 5, wherein the quantifying steps comprise quantitative amplification of the intact copies of the locus.

11. The method of claim 7, wherein the quantitative amplification is real-time quantitative polymerase chain reaction (PCR).

12. The method of claim 7, wherein the method further comprises contacting the genomic DNA with an agent that modifies unmethylated cytosine before the amplification step, and at least one of the two oligonucleotide primers distinguishes between modified unmethylated and methylated DNA in the genomic DNA.

13. The method of claim 12, wherein the agent is sodium bisulfate.

14. The method of claim 2, wherein the quantifying steps comprise detecting a probe that hybridizes to the locus.

15. The method of claim 14, wherein the probe comprises a detectable fluorescent moiety.

16. The method of claim 2, wherein the genomic DNA is from an animal.

17. The method of claim 16, wherein the animal is a human.

18. The method of claim 2, wherein the genomic DNA is from an organism selected from the group consisting of plants, fungi and bacteria.

19. The method of claim 2, wherein the genomic DNA is from a tissue selected from the group consisting of brain tissue, colon tissue, urogenital tissue, lung tissue, renal tissue, breast tissue, thymus tissue, testis tissue, ovarian tissue, and uterine tissue.

* * * * *